(12) United States Patent
Mathies et al.

(10) Patent No.: US 7,799,553 B2
(45) Date of Patent: Sep. 21, 2010

(54) MICROFABRICATED INTEGRATED DNA ANALYSIS SYSTEM

(75) Inventors: Richard A. Mathies, Moraga, CA (US); Robert Blazej, Berkeley, CA (US); Chung Liu, Albany, CA (US); Palani Kumaresan, Berkeley, CA (US); Stephanie H. I. Yeung, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/139,018

(22) Filed: May 25, 2005

(65) Prior Publication Data
US 2005/0287572 A1    Dec. 29, 2005

Related U.S. Application Data

(60) Provisional application No. 60/576,102, filed on Jun. 1, 2004.

(51) Int. Cl.
*C12M 1/00* (2006.01)
*C12M 1/34* (2006.01)
*C12M 3/00* (2006.01)

(52) U.S. Cl. .................. 435/283.1; 204/451; 422/68.1; 435/91.2; 435/287.2; 435/288.6; 536/25.4

(58) Field of Classification Search ................ 204/451; 422/68.1; 435/91.2, 283.1, 287.2, 288.6; 536/25.4
See application file for complete search history.

(56) References Cited

U.S. PATENT DOCUMENTS 3,352,643 A    11/1967    Ando et al.

(Continued)

FOREIGN PATENT DOCUMENTS

EP    0459241 B1    12/1991

(Continued)

OTHER PUBLICATIONS

Soper, S.A., D.C. Williams, Y. Xu, S.J. Lassiter, Y. Zhang, S.M. Ford, and R.C. Bruch, *Sanger DNA sequencing reactions performed in a solid-phase nanoreactor directly coupled to capillary gel electrophoresis*. Anal. Chem., 1998. 70: p. 4036-4043.

(Continued)

*Primary Examiner*—Robert T Crow
*Assistant Examiner*—Narayan K Bhat
(74) *Attorney, Agent, or Firm*—Weaver Austin Villeneuve & Sampson LLP

(57) ABSTRACT

Methods and apparatus for genome analysis are provided. A microfabricated structure including a microfluidic distribution channel is configured to distribute microreactor elements having copies of a sequencing template into a plurality of microfabricated thermal cycling chambers. A microreactor element may include a microcarrier element carrying the multiple copies of the sequencing template. The microcarrier element may comprise a microsphere. An autovalve at an exit port of a thermal cycling chamber, an optical scanner, or a timing arrangement may be used to ensure that only one microsphere will flow into one thermal cycling chamber wherein thermal cycling extension fragments are produced. The extension products are captured, purified, and concentrated in an integrated oligonucleotide gel capture chamber. A microfabricated component separation apparatus is used to analyze the purified extension fragments. The microfabricated structure may be used in a process for performing sequencing and other genetic analysis of DNA or RNA.

16 Claims, 12 Drawing Sheets

U.S. PATENT DOCUMENTS

| | | | |
|---|---|---|---|
| 3,433,257 A | 3/1969 | Jensen | |
| 3,568,692 A | 3/1971 | Metzger et al. | |
| 5,376,252 A | 12/1994 | Ekstrom et al. | |
| 5,453,163 A | 9/1995 | Yan | |
| 5,571,410 A | 11/1996 | Swedberg et al. | |
| 5,587,128 A * | 12/1996 | Wilding et al. | 422/50 |
| 5,705,813 A | 1/1998 | Apffel et al. | |
| 5,741,462 A * | 4/1998 | Nova et al. | 506/37 |
| 5,750,015 A | 5/1998 | Soane et al. | |
| 5,770,029 A | 6/1998 | Nelson et al. | |
| 5,775,371 A | 7/1998 | Pan et al. | |
| 5,856,174 A | 1/1999 | Lipshutz et al. | |
| 5,863,502 A | 1/1999 | Southgate et al. | |
| 5,908,552 A | 6/1999 | Dittmann et al. | |
| 5,922,591 A | 7/1999 | Anderson et al. | |
| 5,942,443 A | 8/1999 | Parce et al. | |
| 5,971,158 A | 10/1999 | Yager et al. | |
| 6,001,229 A | 12/1999 | Ramsey | |
| 6,007,690 A | 12/1999 | Nelson et al. | |
| 6,007,775 A | 12/1999 | Yager | |
| 6,010,607 A | 1/2000 | Ramsey | |
| 6,048,100 A | 4/2000 | Thrall et al. | |
| 6,073,482 A | 6/2000 | Moles | |
| 6,103,199 A | 8/2000 | Bjornson et al. | |
| 6,120,184 A | 9/2000 | Laurence et al. | |
| 6,136,212 A | 10/2000 | Mastrangelo et al. | |
| 6,168,948 B1 | 1/2001 | Anderson et al. | |
| 6,176,962 B1 | 1/2001 | Soane et al. | |
| 6,190,616 B1 | 2/2001 | Jovanovich et al. | |
| 6,207,031 B1 | 3/2001 | Adourian et al. | |
| 6,235,471 B1 | 5/2001 | Knapp et al. | |
| 6,280,589 B1 | 8/2001 | Manz et al. | |
| 6,319,476 B1 | 11/2001 | Victor, Jr. et al. | |
| 6,322,683 B1 | 11/2001 | Wolk et al. | |
| 6,379,929 B1 | 4/2002 | Burns et al. | |
| 6,403,338 B1 | 6/2002 | Knapp et al. | |
| 6,408,878 B2 | 6/2002 | Unger et al. | |
| 6,423,536 B1 | 7/2002 | Jovanovich et al. | |
| 6,432,290 B1 | 8/2002 | Harrison et al. | |
| 6,489,112 B1 | 12/2002 | Hadd et al. | |
| 6,521,188 B1 | 2/2003 | Webster | |
| 6,524,456 B1 | 2/2003 | Ramsey et al. | |
| 6,532,997 B1 * | 3/2003 | Bedingham et al. | 141/1 |
| 6,533,914 B1 | 3/2003 | Liu | |
| 6,537,757 B1 | 3/2003 | Langmore et al. | |
| 6,544,734 B1 | 4/2003 | Briscoe et al. | |
| 6,551,839 B2 | 4/2003 | Jovanovich et al. | |
| 6,581,441 B1 | 6/2003 | Paul | |
| 6,605,454 B2 | 8/2003 | Barenburg et al. | |
| 6,614,228 B2 | 9/2003 | Hofmann et al. | |
| 6,618,679 B2 | 9/2003 | Loehrlein | |
| 6,623,613 B1 | 9/2003 | Mathies et al. | |
| 6,627,446 B1 | 9/2003 | Roach et al. | |
| 6,629,820 B2 | 10/2003 | Kornelsen | |
| 6,632,619 B1 | 10/2003 | Harrison et al. | |
| 6,632,655 B1 | 10/2003 | Mehta et al. | |
| 6,663,833 B1 | 12/2003 | Stave et al. | |
| D486,156 S | 2/2004 | Lee et al. | |
| 6,685,442 B2 | 2/2004 | Chinn et al. | |
| D488,818 S | 4/2004 | Lee et al. | |
| 6,752,922 B2 | 6/2004 | Huang et al. | |
| 6,764,648 B1 | 7/2004 | Roach et al. | |
| 6,782,746 B1 | 8/2004 | Hasselbrink et al. | |
| 6,786,708 B2 | 9/2004 | Brown et al. | |
| 6,787,111 B2 | 9/2004 | Roach et al. | |
| 6,793,753 B2 | 9/2004 | Unger et al. | |
| 6,802,342 B2 | 10/2004 | Fernandes et al. | |
| 6,803,019 B1 | 10/2004 | Bjornson et al. | |
| 6,824,663 B1 | 11/2004 | Boone | |
| 6,829,753 B2 | 12/2004 | Lee et al. | |
| 6,852,287 B2 | 2/2005 | Ganesan | |
| 6,870,185 B2 | 3/2005 | Roach et al. | |
| 6,885,982 B2 | 4/2005 | Harris et al. | |
| 6,899,137 B2 | 5/2005 | Unger et al. | |
| 6,923,907 B2 | 8/2005 | Hobbs et al. | |
| 6,929,030 B2 | 8/2005 | Unger et al. | |
| 6,951,632 B2 | 10/2005 | Unger et al. | |
| 6,953,058 B2 | 10/2005 | Fernandes et al. | |
| 6,960,437 B2 | 11/2005 | Enzelberger et al. | |
| 7,005,493 B2 | 2/2006 | Huang et al. | |
| 7,015,030 B1 | 3/2006 | Fouillet et al. | |
| 7,198,759 B2 | 4/2007 | Bryning et al. | |
| 7,312,611 B1 | 12/2007 | Harrison et al. | |
| 7,323,305 B2 * | 1/2008 | Leamon et al. | 435/6 |
| 7,438,856 B2 | 10/2008 | Jedrzejewski et al. | |
| 7,488,603 B2 | 2/2009 | Gjerde et al. | |
| 2002/0022587 A1 | 2/2002 | Ferguson et al. | |
| 2002/0047003 A1 * | 4/2002 | Bedingham et al. | 219/388 |
| 2002/0048536 A1 | 4/2002 | Bergh et al. | |
| 2002/0051992 A1 | 5/2002 | Bridgham et al. | |
| 2002/0058332 A1 * | 5/2002 | Quake et al. | 435/288.3 |
| 2002/0098097 A1 | 7/2002 | Singh | |
| 2002/0110900 A1 | 8/2002 | Jovanovich et al. | |
| 2002/0119480 A1 | 8/2002 | Weir et al. | |
| 2002/0119482 A1 | 8/2002 | Nelson et al. | |
| 2003/0021734 A1 * | 1/2003 | Vann et al. | 422/100 |
| 2003/0217923 A1 | 11/2003 | Harrison et al. | |
| 2004/0014091 A1 * | 1/2004 | Duck et al. | 435/6 |
| 2004/0037739 A1 | 2/2004 | Mcneely et al. | |
| 2004/0053290 A1 | 3/2004 | Terbrueggen et al. | |
| 2004/0063217 A1 | 4/2004 | Webster et al. | |
| 2004/0072278 A1 | 4/2004 | Chou et al. | |
| 2004/0086872 A1 | 5/2004 | Childers et al. | |
| 2004/0132170 A1 | 7/2004 | Storek et al. | |
| 2004/0151629 A1 | 8/2004 | Pease et al. | |
| 2004/0197845 A1 | 10/2004 | Hassibi et al. | |
| 2004/0209354 A1 | 10/2004 | Mathies et al. | |
| 2004/0224380 A1 | 11/2004 | Chou et al. | |
| 2005/0047967 A1 | 3/2005 | Chuang et al. | |
| 2005/0053952 A1 | 3/2005 | Hong et al. | |
| 2005/0161326 A1 | 7/2005 | Morita et al. | |
| 2005/0224134 A1 | 10/2005 | Yin et al. | |
| 2005/0224352 A1 | 10/2005 | Harrison et al. | |
| 2005/0255003 A1 | 11/2005 | Summersgill et al. | |
| 2005/0287572 A1 | 12/2005 | Mathies et al. | |
| 2006/0027456 A1 | 2/2006 | Harrison et al. | |
| 2006/0057209 A1 | 3/2006 | Chapman et al. | |
| 2006/0073484 A1 | 4/2006 | Mathies et al. | |
| 2006/0076068 A1 | 4/2006 | Young et al. | |
| 2006/0163143 A1 | 7/2006 | Chirica et al. | |
| 2006/0186043 A1 | 8/2006 | Covey et al. | |
| 2006/0266645 A1 | 11/2006 | Chen et al. | |
| 2007/0017812 A1 | 1/2007 | Bousse | |
| 2007/0175756 A1 | 8/2007 | Nguyen et al. | |
| 2007/0237686 A1 | 10/2007 | Mathies et al. | |
| 2007/0248958 A1 | 10/2007 | Jovanovich et al. | |
| 2007/0297947 A1 | 12/2007 | Sommers et al. | |
| 2008/0014576 A1 | 1/2008 | Jovanovich et al. | |
| 2008/0237146 A1 | 10/2008 | Harrison et al. | |
| 2009/0035770 A1 | 2/2009 | Mathies et al. | |
| 2009/0060797 A1 | 3/2009 | Mathies et al. | |
| 2009/0084679 A1 | 4/2009 | Harrison et al. | |

FOREIGN PATENT DOCUMENTS

| | | |
|---|---|---|
| EP | 0527905 | 11/1995 |
| EP | 1065378 | 4/2002 |
| JP | 408327594 A | 12/1996 |
| WO | WO 96/04547 A1 | 2/1996 |
| WO | WO 98/52691 A1 | 11/1998 |
| WO | WO 99/36766 A1 | 7/1999 |
| WO | WO 99/40174 A1 | 8/1999 |
| WO | WO00/40712 | 7/2000 |
| WO | WO 00/40712 * | 7/2000 |

| WO | WO 00/60362 A1 | 10/2000 |
| WO | WO 01/38865 A1 | 5/2001 |
| WO | WO 01/85341 A1 | 11/2001 |
| WO | WO 02/43615 | 6/2002 |
| WO | WO 02/43615 A3 | 6/2002 |
| WO | WO 2004/098757 A2 | 11/2004 |
| WO | WO 2004/098757 A3 | 11/2004 |
| WO | WO 2005/075081 A1 | 8/2005 |

OTHER PUBLICATIONS

Hultman, T., S. Bergh, T. Moks, and M. Uhlén, *Bidirectional solid-phase sequencing of in vitro-amplified plasmid DNA*. BioTechniques, 1991. 10: p. 84-93.

Nakano, H., K. Kobayashi, S. Ohuchi, S. Sekiguchi, and T. Yamane, *Single-step single-molecule PCR of DNA with a homo-priming sequence using a single primer and hot-startable DNA polymerase*. Journal of Bioscience and Bioengineering, 2000. 90(4): p. 456-458.

Mitra, R.D., V.L. Butty, J. Shendure, B.R. Williams, D.E. Housman, and G.M. Church, *Digital genotyping and haplotyping with polymerase colonies*. Proceedings of the National Academy of Sciences of the United States of America, 2003. 100(10): p. 5926-5931.

Dressman, D., H. Yan, G. Traverso, K.W. Kinzler, and B. Vogelstein, *Transforming single DNA molecules into fluorescent magnetic particles for detection and enumeration of genetic variations*. Proceedings of the National Academy of Sciences of the United States of America, 2003. 100(15): p. 8817-8822.

Brenner, S., et al., *Gene expression analysis by massively parallel signature sequencing (MPSS) on microbead arrays*. Nature Biotechnology, 2000. 18(6): p. 630-634.

Paegel, B.M., S.H.I. Yeung, and R.A. Mathies, *Microchip bioprocessor for integrated nanovolume sample purification and DNA sequencing*. Analytical Chemistry, 2002. 74: p. 5092-5098.

Paegel, B.M., R.G. Blazej, and R.A. Mathies, *Microfluidic devices for DNA sequencing sample preparation and electrophoresis analysis*. Current Opinions in Biotechnology, 2003. 14: p. 42-50.

Liu, S., Y. Shi, W.W. Ja, and R.A. Mathies, *Optimization of high-speed DNA sequencing on microfabricated capillary electrophoresis channels*. Anal. Chem., 1999. 71: p. 566-573.

Leamon, J.H., W.L. Lee, K.R. Tartaro, J.R. Lanza, G.J. Sarkis, A.D. deWinder, J. Berka, and K.L. Lohman, *A massively parallel Pico Titer Plate (TM) based platform for discrete picoliter-scale polymerase chain reactions*. Electrophoresis, 2003. 24: p. 3769-3777.

Ghadessy, F.J., J.L. Ong, and P. Holliger, *Directed evolution of polymerase function by compartmentalized self-replication*. PNAS, 2001. 98: p. 4552-4557.

Rye, H.S., M.A. Quesada, K. Peck, R.A. Mathies, and A.N. Glazer, *High-sensitivity two-color detection of double-stranded DNA with a confocal fluorescence gel scanner using ethidium homodimer and thiazole orange*. Nucleic Acids Res., 1991. 19: p. 327-333.

Fleming, N., J. Maynard, L. Tzitzis, J.R. Sampson, and J.P. Cheadle, *LD-PCR coupled to long-read direct sequencing: an approach for mutation detection in genes with compact genomic structures*. Journal of Biochemical and Biophysical Methods, 2001. 47(1-2): p. 131-136.

Blazej, R.G., B.M. Paegel, and R.A. Mathies, *Polymorphism ratio sequencing: A new approach for single nucleotide polymorphism discovery and genotyping*. Genome Research, 2003. 13: p. 287-293.

Kamei, T., B.M. Paegel, J.R. Scherer, A.M. Skelley, R.A. Street, and R.A. Mathies, *Integrated Hydrogenated Amorphous Si Photodiode Detector for Microfluidic Bioanalytical Devices*. Analytical Chemistry, 2003. 75: p. 5300-5305.

Simpson, P.C., A.T. Woolley, and R.A. Mathies, *Microfabrication technology for the production of capillary array electrophoresis chips*. Biomedical Microdevices, 1998. 1(1): p. 7-26.

Grover, W.H., A.M. Skelley, C.N. Liu, E.T. Lagally, and R.A. Mathies, *Monolithic membrane valves and diaphragm pumps for practical large-scale integration into microfluidic devices*. Sensors & Actuators B, 2003. 89: p. 315-323.

Lagally, E.T., C.A. Emrich, and R.A. Mathies, *Fully integrated PCR-capillary electrophoresis microsystem for DNA analysis*. Lab on a Chip, 2001. 1(2): p. 102-107.

Paegel, B.M., C.A. Emrich, G.J. Wedemayer, J.R. Scherer, and R.A. Mathies, *High-throughput DNA sequencing with a 96-Lane capillary array electrophoresis bioprocessor*. Proceedings of the National Academy of Science, U.S.A., 2002. 99: p. 574-579.

Albarghouthi, M.N., B.A. Buchholz, P.J. Huiberts, T.M. Stein, and A.E. Barron, *Poly-N-hydroxyethylacrylamide (polyDuramide): A Novel hydrophilic self-coating polymer matrix for DNA sequencing by capillary electrophroesis*. Electrophoresis, 2002. 23: 1429-1440.

Kan, C.W., E.A.S. Doherty, and A.E. Barron, *A novel thermogelling matrix for microchannel DNA sequencing based on poly-N-alkoxyalkylacrylamide copolymers*. Electrophoresis, 2003. 24(24): p. 4161-4169.

Doherty, E.A.S., C.W. Kan, and A.E. Barron, *Sparsely cross-linked "nanogels" for microchannel DNA sequencing*. Electrophoresis, 2003. 24(24): p. 4170-4180.

Doherty, E.A.S., C.W. Kan, B.M. Paegel, S.H.I. Yeung, S. Cao, R.A. Mathies, and A.E. Barron, *Sparsely crosslinked "nanogel" matrices as fluid, mechanically stablized polymer networks for high-throughput microchannel DNA sequencing*. Analytical Chemistry (manuscript submitted)., 2004.

Giddings, M.C., J. Severin, M. Westphall, J. Wu, and L.M. Smith, *A software system for data analysis in automated DNA sequencing*. Genome Research, 1998. 8: p. 644-665.

Ewing, B., L. Hillier, M.C. Wendl, and P. Green, *Base-calling of automated sequencer traces using Phred*. Genome Research, 1998. 8: p. 175-194.

Ewing, B. and P. Green, *Base-calling of automated sequencer traces using phred. II. Error probabilities*. Genome Research, 1998. 8: p. 186-194.

Buchholz, B.A. and A.E. Barron, *The use of light scattering for precise characterization of polymers for DNA sequencing by capillary electrophoresis*. Electrophoresis, 2001. 22: p. 4118-4128.

Lagally, E. T. et al. Integrated Portable Genetic Analysis Microsystem for Pathogen/Infectious Disease Detection. *Analytical Chemistry* 76, 3162-3170 (2004).

Paegel, B. M., Yeung, S. H. I. & Mathies, R. A. Microchip bioprocessor for integrated nanovolume sample purification and DNA sequencing. *Analytical Chemistry* 74, 5092-5098 (2002).

Paegel, B. M., Emrich, C. A., Wedemayer, G. J., Scherer, J. R. & Mathies, R. A. High-throughput DNA sequencing with a 96-Lane capillary array electrophoresis biopressor. *PNAS*, 99, 574-579 (2002).

Doherty, E. A. S., Kan, C.-W. & Barron, A. E. Sparsely crosslinked "nanogels" for microchannel DNA sequencing. *Electrophoresis* 24, 4170-4180 (2003).

Grover, W. H., Skelley, A. M., Liu, C. N., Lagally, E. T. & Mathies, R. A. Monolithic membrane valves and diaphragm pumps for practical large-scale integration into microfluidic devices. *Sensors & Actuators B* 89, 315-323 (2003).

Vazquez, M. et al. Electrophoretic injection within microdevices. *Analytical Chemistry* 74, 1952-1961 (2002).

Giddings, M., Severlin, J., Westphall, M., Wu, J. & Smith, L. A software system for data analysis in automated DNA sequencing. *Genome Research* 8, 644-665 (1998).

Doherty, E. A. S. et al. Sparsely Crosslinked "Nanogel" Matrixes as Fluid, Mechanically Stabilized Polymer Networks for High-Throughput Microchannel DNA Sequencing. *Analytical Chemistry* 76, 5249-5256 (2004).

Song, H., Tice, J. D. & Ismagilov, R. F. A microfluidic system for controlling reaction networks in time. *Angewandte Chemie-International Edition* 42, 768-772 (2003).

Lagally, E. T., Emrich, C. A. & Mathies, R. A. Fully Integrated PCR-Capillary Electrophoresis Microsystem for DNA Analysis. *Lab-on-a-Chip* 1, 102-107 (2001).

Srinivasan, U., Houston, M. R., Howe, R. T. & Maboudian, R. Alkyltrichlorosilane-based self-assembled monolayer films for stiction reduction in silicon micromachines. *Journal of Microelectromechanical Systems* 7, 252-260 (1998).

Tice, J. D., Song, H., Lyon, A. D. & Ismagilov, R. F. Formation of droplets and mixing in multiphase microfluidics at low values of the Reynolds and the capillary numbers. *Langmuir* 19, 9127-9133 (2003).

Peter C. Simpson, et al., High-throughput genetic analysis using microfabricated 96-sample capillary array electrophoresis microplates, *Proc. Natl. Acad. Sci. USA*, vol. 95, pp. 2256-2261, Mar. 1998 Biophysics.

Pierre J. Obeid, et al., Microfabricated Device for DNA and RNA Amplification by Continuous-Flow Polymerase Chain Reaction and Reverse Transcription-Polymerase Chain Reaction With Cycle Number Selection, *Anal. Chem.* 2003, vol. 75, No. 2, Jan. 15, 2003, pp. 288-295.

Nokyoung Park, et al., Cylindrical Compact Thermal-Cycling Device for Continuous-Flow Polymerase Chain Reaction, *Anal. Chem.*, vol. 75, No. 21, Nov. 1, 2003, pp. 6029-6033.

Mario Curcio, et al., Continuous Segmented-Flow Polymerase Chain Reaction for High-Throughput Miniaturized DNA Amplification, *Anal. Chem.*, vol. 75, No. 1, Jan. 1, 2003, pp. 1-7.

Kevin D. Dorfman, et al., Contamination-Free Continuous Flow Microfluidic Polymerase Chain Reaction for Quantitative and Clinical Applications, *Anal. Chem.*, (Technical Note); 2005 77(11); 3700-3704.

U.S. Appl. No. 10/750,533, filed Dec. 29, 2003, by Richard A. Mathies, et al., for Fluid Control Structures in Microfluidic Devices.

Thorsen et al., "Microfludic Large-Scale Integration", *Science*, vol. 298, Oct. 18, 2002, pp. 580-584.

Grover et al., *Practical Valves and Pumps for Large-Scale Integration into Microfludic Analysis Devices*. Micro Total Analysis Systems (Nov. 2002), 2 pages.

Grover et al., *Practical Valves and Pumps for Large-Scale Integration into Microfludic Analysis Devices*. Micro Total Analysis Systems (Nov. 2002), 2 pages.

D.J. Harrison, et al., Micromachining a miniaturized capillary electrophoresis-based chemical analysis system on a chip, *Science*, 261(5123): 895-897, 1993.

C.A. Emrich, et al., Microfabricated 384-lane capillary array electrophoresis bioanalyzer for ultrahigh-throughput genetic analysis, *Analytical Chemistry*, 74(19): 5076-5083, 20.

E.T. Lagally, et al., Monolithic integrated microfluidic DNA amplification and capillary electrophoresis analysis system, *Sensors and Actuators B-Chemical*, 63(3): 138-146, 2000.

T. Ohori, et al., Partly disposable three-way mirovalve for a medical micro total analysis system (muTAS), *Sensors and Actuators A-Physical*, 64(1): 57-62, 1998.

X. Yang, et al., A MEMS Thermopneumatic Silicone rubber membrane valve, *Sensors and Actuators A-Physical*, 64(1): 101-108, 1998.

Rolfe C. Anderson, et al., A miniature integrated device for automated multistep genetic assays, *Nucleic Acids Research*, 28(12): e60, 2000.

M.A. Unger, et al., Monolithic microfabricated valves and pumps by multilayer soft lithography, *Science*, 188(5463): 113-116, 2000.

E.T. Lagally, et al., Single-molecule DNA amplification and analysis in an integrated microfluidic device, *Analytical Chemistry*, 73(3): 565-570, 2001.

R.A. Mathies, et al., Capillary array electrophoresis bioprocessors, *Solid-State Sensor, Actuator and Microsystems Workshop*, pp. 112-117, HIlton Head Island, SC, USA, 2002.

C.L. Hansen, et al., A robust and scalable microfluidic metering method that allows protein crystal growth by free interface diffusion, *Proceedings of the National Academy of Science*, 99(26):16531-16536, 2002.

Weimer, B.C., et al., Solid-phase capture of proteins, spores and bacteria, *App. Environ. Microbiology*, 67:1300-1307 (2001).

Yu, C., et al., Towards stationary phases for chromatography on a microchip: Molded porous polymer monoliths prepared in capillaries by photoinitiated in situ polymerization as separation media for electrochromatography, *Electrophoresis*, 21:120-127 (2000).

Yu, C., et al., Preparation of monolithic polymers with controlled porous properties for microfluidic chip applications using photoinitiated free radial polymerization, *J. Polymer Sci.*, 40:755 (2002).

Rohr, T., et al., Porous Polymer Monoliths: Simple and Efficient Mixers Prepared By Direct Polymerization in the channels of Microfludic Chips, *Electrophoresis*, 22:3959-3967 (2001).

Peterson, D.S., et al., Enzymatic Microreactor-on-a-Chip: Protein Mapping Using Trypsin Immobilized on Porous Polymer Monoliths Molded in Channels of Microfluidic Devices, *Anal. Chem.* 74:4081-4088 (2002).

Woolley, A.T., et al., Functional Integration of PCR Amplification and Capillary Electrophoresis in a Microfabricated DNA Analysis Device, *Anal. Chem.*, 68:4081-4086 (1999).

Waller et al., "*Quantitative Immunocapture PCR Assay for Detection of Campyllobacter jejuni in Foods*," Applied and Environmental Microbiology, Sep. 2000, vol. 66, No. 9, pp. 4115-4118.

Office Action mailed Jul. 12, 2007 in U.S. Appl. No. 10/750,533, filed Dec. 29, 2003.

Office Action mailed Jul. 7, 2007 in U.S. Appl. No. 10/540,658, filed Jun. 23, 2005.

PCT Search Report, Pct Application No. PCT/US05/18678, Mailed Sep. 28, 2007.

PCT Written Opinion, Pct Application No. PCT/US05/18678, Mailed Sep. 28, 2007.

Amendment and Request for Correction of Inventorship mailed Jan. 10, 2008 in U.S. Appl. No. 10/750,533.

Bings, et al. Microfluidic Devices Connected to Fused-Silica Capillaries with Minimal Dead Dead Volume. Analytical Chemistry. 1999;71(15):3292-3296.

Blazej, et al. Microfabricated bioprocessor for integrated nanoliter-scale Sanger DNA sequencing. Proc. Natl. Acad. Sci. USA 2006;103:7240-7245.

CAPLUS abstract of Krohkin et al. Modified silica as a stationary phase for ion chromatography. Journal of Chromatography A. 1995;706:93-8.

Chan, et al. Microfabricated Polymer Devices for Automated Sample Delivery of Peptides for Analysis by Electrospray Ionization Tandem Mass Spectrometry. Analytical Chemistry. 1999;71(20):4437-4444.

Chiem, et al. Microchip systems for immunoassay: an integrated immunoreactor with electrophoretic separation for serum theophylline determination. Clinical Chemistry.1998;44(3):591-598.

Chiem, et al. Room temperature bonding of micromachined glass devices for capillary electrophoresis. Sensors and Actuators. 2000;B63(3):147-152.

Coleman, et al. A sequential injection microfluidic mixing strategy. Microfluidics and Nanofluidics. 2005;319-327.

Diehl, et al. BEAMing: single-molecule PCR on microparticles in water-in-oil emulsions. Nature Methods. 2006;3(7):551-9.

Doyle, et al. Self-Assembled Magnetic Matrices for DNA Separation Chips. Science. 2000;295:2237.

Ericson, et al. Electroosmosis- and Pressure-Driven Chromatography in Chips Using Continuous Beds. Analytical Chemistry. 2000;72(1):81-87.

Figeys, et al. A Microfabricated Device for Rapid Protein Identification by Microelectrospray Ion Trap Mass Spectrometry. Analytical Chemistry. 1997;69(16):3153-3160.

Figeys, et al. An Integrated Microfluidics-Tandem Mass Spectrometry System for Automated Protein Analysis. Analytical Chemistry. 1998;70(18):3728-3734.

Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.

Figeys, et al. Nanoflow Solvent Gradient Delivery from a Microfabricated Device for Protein Identifications by Electrospray Ionization Mass Spectrometry. Analytical Chemistry. 1998;70(18):3721-3727.

Francis, et al. Flow analysis based on a pulsed flow of solution: theory, instrumentation and applications. Talanta. 2002;58(6):1029-1042.

Ghadessy, et al. Directed evolution of polymerase function by compartmentalized self-replication. Proc Natl Acad Sci USA. 2001;98:4552-4557.

Goll, et al. Microvalves with bistable buckled polymer diaphragms. Journal of Micromechanics and Microengineering. 1996;6:77-79.

Grover, et al. Development and multiplexed control of latching pneumatic valves using microfluidic logical structures. Lab on a chip. 2006;6:623-631.

Grover, et al. An integrated microfluidic processor for single nucleotide polymorphism-based DNA computing. Lab on a Chip. 2005;5(10):1033-1040.

Hayes, et al. EDGE: A Centralized Resource for the Comparison, Analysis, and Distribution of Toxicogenomic Information. Molecular Pharmacology. 2005;67(4):1360-1368.

International Preliminary Report for corresponding PCT Application No. PCT/CA2000/01421 dated Feb. 14, 2002.

International Preliminary Report for corresponding PCT Application No. PCT/US2005/018678 dated Nov. 13, 2007.

International Preliminary Report for corresponding PCT Application No. PCT/US2005/033347 dated Mar. 20, 2007.

International Preliminary Report for corresponding PCT Application No. PCT/US2007/007381 dated Sep. 23, 2008.

International Preliminary Report for corresponding PCT Application No. PCT/US2007/02721 dated Aug. 5, 2008.

International Preliminary Report for corresponding PCT Application No. PCT/US2007/061573 dated Aug. 26, 2008.

International Search Report for PCT/US2005/033347.

Ju, et al. Fluorescence energy transfer dye-labeled primers for DNA sequencing and analysis. Proc. Natl. Acad. Sci. USA. 1995;92:4347-4351.

Koh, et al. Integrating Polymerase Chain Reaction, Valving, and Electrophoresis in a Plastic Device for Bacterial Detection. Analytical Chemistry. 2003;75(17):4591-4598.

Kopp, et al. Chemical Amplification Continuous-Flow PCR on a Chip. Science. 1998;280:1046-1048.

Lazar, et al. Subattomole-Sensitivity Microchip Nanoelectrospray Source with Time-of-Flight Mass Spectrometry Detection. Analytical Chemistry. 1999;71(17):3627-3631.

Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.

Li, et al. Rapid and sensitive separation of trace level protein digests using microfabricated devices coupled to a quadrupole—time-of-flight mass spectrometer. Electrophoresis. 2000;21:198-210.

Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.

Licklider, et al. A Micromachined Chip-Based Electrospray Source for Mass Spectrometry. Analytical Chemistry. 2000;72(2):367-375.

Lisec, et al. A bistable pneumatic microswitch for driving fluidic components. Sensors and Actuators. 1996;A54:746-749.

Liu, et al. Automated parallel DNA sequencing on multiple channel microchips. Proc. Natl. Acad. Sci. USA. 2000;97(10):5369-5374.

Margulies, et al. Genome sequencing in microfabricated high-density picolitre reactors. Nature. 2005;437(7057):376-80. (Abstact only).

Melin, et al. A Passive 2-Dimensional Liquid Sample Micromixer. 7th International Conference on Miniaturized Chemical and Biochemical Analysis Systems. 2003;167-170.

Ocvirk, et al. High Performance Liquid Chromatography Partially Integrated onto a Silicon Chip. Analytical Methods and Instrumentation. 1995;2:74-82.

Ocvirk, et al. Optimization of confocal epifluorescence microscopy for microchip-based miniaturized total analysis systems. The Analyst. 1998;123:1429-1434.

Office Action Final dated Feb. 19, 2008 issued in U.S. Appl. No. 10/540,658.

Office Action mailed Jul. 2, 2007 in U.S. Appl. No. 10/540,658, filed Jun. 23, 2005.

Oleschuk, et al. Trapping of Bead-Based Reagents within Microfluidic Systems: On-Chip Solid-Phase Extraction and Electrochromatography. Analytical Chemistry. 2000;72:585-590.

Olsen, et al. Immobilization of DNA Hydrogel Plugs in Microfluidic Channels. Analytical Chemistry. 2002;74:1436-1441.

Paegel, et al. Turn Geometry for Minimizing Band Broadening in Microfabricated Capillary Electrophoresis Channels. Analytical Chemistry. 2000;72:3030-3037.

PCT Notification of Transmittal of the International Search Report and The Written Opinion of the International Searching Authority, or the Declaration, mailed Jun. 17, 2008, Application No. PCT/US2007/082568.

Ramsey, et al. Generating Electrospray from Microchip Devices Using Electroosmotic Pumping. Analytical Chemistry. 1997;69(6):1174-1178.

Scherer, et al. High-Pressure Gel Loader for Capillary Array Electrophoresis Microchannel Plates. Biotechniques. 2001;31(5):1150-1154.

Schomburg, et al. Design Optimization of Bistable Microdiaphragm Valves. Sensors and Actuators. 1998;A64:259-264.

Simpson, et al. High-throughput genetic analysis using microfabricated 96-sample capillary array electrophoresis microplates. Proc Natl Acad Sci USA. 1998;95:2256-2261.

Spiering, et al. Novel microstructures and technologies applied in chemical analysis techniques. 1997 International Conference on Solid-State Sensors and Actuators. 1997;1:511-514.

Takao, et al. A Pneumatically Actuated Full In-Channel Microvalve With MOSFET-Like Function in Fluid Channel Networks. Journal of Microelectromechanical Systems. 2002;11(5):421-426.

Takao, et al. Microfluidic Integrated Circuits for Signal Processing Using Analogous Relationship Betweeen Pneumatic Microvalve and MOSFET. Journal of Microelectromechanical Systems. 2003;12(4):497-505.

Thomas, et al. Application of Genomics to Toxicology Research. Environmental Health Perspectives. 2002;110(6):919-923.

Van Der Moolen, et al. A Micromachined Injection Device for CZE: Application to Correlation CZE. Analytical Chemistry. 1997;69(20):4220-4225.

Van Der Moolen, et al. Correlation Capillary Zone Electrophoresis, a Novel Technique to Decrease Detection Limits. Chromatographia. 1995;40(7/8):368-374.

Veenstra, et al. The design of an in-plane compliance structure for microfluidical systems. Sensors and Actuators. 2002;B81:377-383.

Wen, et al. Microfabricated isoelectric focusing device for direct electrospray ionization-mass spectrometry. Electrophoresis. 2000;21:191-197.

Wikipedia brochure for defining stocahstic process. Sep. 2, 2009.

Williams, et al. Amplification of complex gene libraries by emulsion PCR. Nature Methods. 2006;3(7):545-50.

Wright, et al. Behavior and Use of Nonaqueous Media without Supporting Electrolyte in Capillary Electrophoresis and Capillary Electrochromatography. Analytical Chemistry. 1997;69(16):3251-3259.

Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.

Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.

Xue, et al. Multichannel Microchip Electrospray Mass Spectrometry. Analytical Chemistry. 1997;69(3):426-430.

Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.

Zhang, et al. Microfabricated Devices for Capillary Electrophoresis-Electrospray Mass Spectrometry. Analytical Chemistry. 1999;71(15):3258-3264.

Chinese Office Action dated Jan. 25, 2008, from Application No. 2003801100666.

Ligler, F.S., et al., "Integrating Waveguide Biosensor," Anal. Chem., 2002, vol. 74, pp. 713-719.

Notice of Allowance and Fees Due mailed Aug. 13, 2008 from U.S. Appl. No. 10/750,533.

Allowed Claims from U.S. Appl. No. 10/750,533.

Office Action dated Oct. 8, 2008 issued in U.S. Appl. No. 10/540,658.

Office Action Final dated Mar. 2, 2009 issued in U.S. Appl. No. 10/540,658.

International Search Report and the Written Opinion of the International Searching Report Oct. 29, 2007, Application No. PCT/US2005/018678.

Mathies, et al., U.S. Appl. No. 10/750,533, titled "Fluid Control Structures in Microfluidic Devices," filed Dec. 29, 2003.

Mathies, et al., U.S. Appl. No. 10/540,658, titled "Methods and Apparatus for Pathogen Detection and Analysis, " filed Jun. 23, 2005.

Mathies, et al., U.S. Appl. No. 11/726,701, titled "Multiplexed Latching Valves for Microfluidic Devices and Processors," filed Mar. 21, 2007.

PCT Notification of Transmittal of the International Search Report and the Written Opinion of the International Searching Authority, or the Declaration, mailed Jul. 15, 2008, Application No. PCT/US2007/007381.

Hidekuni, T., et al. Pneumatically Actuated Full in Channel Microvalve With MOSFET—Like Function IN Fluid Channel Networks, Journal of Microelectromechanical Systems, 2002, 11:5; 421-426. P066).

Hidekuni, T., et al., Microfluidic Integrated Circuits for Signal Processing Using Analogous Relationship Between Pneumatic Microvalve and MOSFET, Journal of Microelectromechanical System 2003, 12:4; 497-505.

Mircea, C., et al., Design Fabrication and Testing of a Bistable Electromagnetically Actuated Microvalve. Journal of Microeclectromechanical System 2000. vol. 9; 181-189.

Press, W., et al., An Integrated Microfluidic Processor for Single Nucleotide Polymorphism-based DNA Computing, Lab on a Chip. 2005, 5:10, 8 pages.

Roth, C. et al., Fundamentals of Logic Design, $3^{rd}$ Edition, West Publishing Company, 1985 (Table of Content).

* cited by examiner

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence

```
-continued

<220> FEATURE:
<223> OTHER INFORMATION: Selected as an example in the study of the
      operation of the MINDS system

<400> SEQUENCE: 1
actggccgtc gttttacaa                                                      19

<210> SEQ ID NO 2
<211> LENGTH: 30
<212> TYPE: DNA
<213> ORGANISM: Artificial Sequence
<220> FEATURE:
<223> OTHER INFORMATION: Selected as an example in the study of the
      operation of the MINDS system

<400> SEQUENCE: 2
ttctggtgcc ggaaaccagg caaagcgcca                                          30

<210> SEQ ID NO 3
<211> LENGTH: 28
<212> TYPE: DNA
<213> ORGANISM: Artificial Sequence
<220> FEATURE:
<223> OTHER INFORMATION: Selected as an example in the study of the
      operation of the MINDS system

<400> SEQUENCE: 3
acgcgcagcg tgaccgctac acttgcca                                            28
```

MICROFABRICATED INTEGRATED DNA ANALYSIS SYSTEM

CROSS REFERENCE TO RELATED APPLICATIONS

This application claims priority under 35 U.S.C. 119(e) from Provisional U.S. Patent Application Ser. No. 60/576,102, filed Jun. 1, 2004, entitled "MICROBEAD INTEGRATED DNA ANALYSIS SYSTEM (MINDS)", which is incorporated herein by reference.

STATEMENT REGARDING FEDERALLY SPONSORED RESEARCH

This invention was made with government support under Grant Numbers AI056472, CA77664, and HG001399 awarded by the National Institute of Health. The government has certain rights in the invention.

BACKGROUND

1. Field of Invention

The present invention relates to microfabricated and microfluidic structures. In one example, the present invention relates to a microfabricated system and method for genome sequencing.

2. Description of Related Art

The genome of an organism is defined by the DNA (deoxyribonucleic acid) or, for some viruses, the RNA (ribonucleic acid) of the organism. Genome sequencing is figuring out the order of the nucleotides, or bases, of a DNA or RNA strand.

A current approach to genome-scale sequencing of DNA is shown in FIG. 1. This shotgun sequencing approach 100 uses bacterial transformation, selection and growth to manipulate individual genomic DNA fragments. The first three steps of this approach, shearing, vector ligation, and transformation (steps 102, 104, and 106), need only be performed once. As such, they do not present any particular problems. The last step, the capillary electrophoresis (CE) (step 114), has been miniaturized through microfabrication. This has reduced the cost and processing time associated with this step. The plate and grow (step 108), and the pick, grow and extract steps (step 110), however, are problematic. These steps, which precede the Sanger extension step (step 112), perform clone isolation and insert amplification. The amplification may be bacterial, PCR (polymerase chain reaction) or RCA (rolling circle amplification). These steps have remained refractory to miniaturization and integration. The current macroscopic paradigm has thus relied upon the use of robotics as the enabling technology for these key steps. However, this is a problem because no less than 30 million colonies must be picked and grown to produce a sequencing template for a genome. Furthermore, the minimum quantities of materials prepared by such robotic technologies are orders of magnitude more than that required by modern microfabricated CE analysis systems.

Therefore, it is desirable to improve the processing time, volume scale, and level of integration of genome sequencing. It is also desirable to reduce the cost and space requirements of genome sequencing.

SUMMARY

In one aspect, the invention features a microfabricated structure including a distribution channel to distribute microreactor elements carrying multiple copies of a clonal sequencing template into a plurality of thermal cycling chambers. Only one microreactor element is passed into one thermal cycling chamber wherein thermal cycling extension fragments are produced from a microreactor element. Purification chambers are connected to the thermal cycling chambers to capture and concentrate the extension fragments. Component separation channels are connected to the purification chambers to analyze the extension fragments.

Various implementations of the invention may include one or more of the following features. The microreactor includes a microcarrier element that carries the multiple copies of the clonal sequencing template. The microreactor element is a bolus or microemulsion droplet. The microreactor element includes a microsphere carrying the multiple copies of the clonal sequencing template. The sequencing template is a DNA or RNA sequencing template.

In yet another aspect, the invention is directed to a system for performing sequencing. The system includes a means for shearing DNA or RNA into fragments and means for ligating the fragments to form a mixture of desired circular and contaminating linear products. The system further includes means for selectively removing the contaminating linear products and means for generating microreactor elements carrying multiple clonal copies of a single sequencing template. The system also includes means for selecting which microreactor elements have a sequencing template and microfluidic distribution means for distributing a selected microreactor element with a sequencing template into a thermal cycling chamber. Additionally, the system includes means for ensuring that only one microreactor element will flow into one thermal cycling chamber and extension means, including the thermal cycling chambers, for producing thermal cycling extension fragments from the microreactor elements carrying multiple copies of the sequencing template. Purification chamber means for capturing, purifying and concentrating the extension fragments, and component separation means for analyzing the extension fragments are also part of the system.

Other implementations of the invention may include one or more of the following features. The microreactor element includes a microcarrier element that carries the multiple copies of the clonal sequencing template. The microreactor element is a bolus or a microemulsion droplet. The microreactor element includes a microsphere carrying the multiple copies of the sequencing template.

In another aspect, the invention features a microfabricated structure including a distribution channel to distribute microspheres carrying multiple copies of a clonal sequencing template into a plurality of thermal cycling chambers. An autovalve is located at an exit port of a thermal cycling chamber to ensure that only one microsphere will flow into one thermal cycling chamber wherein thermal cycling extension fragments are produced from the microsphere. Purification chambers are connected to the thermal cycling chambers to capture and concentrate the extension fragments. Component separation channels are connected to the purification chambers to analyze the extension fragments.

Various implementations of the invention may include one or more of the following features. The diameter of a microsphere is between about 1 and 100 microns. The diameter of a microsphere is about 10 microns. Each thermal cycling chamber is in fluid communication with a separation channel. The sequencing template is a DNA or RNA sequencing template.

In still another aspect, the invention is directed to a microfabricated structure including a microfluidic distribution channel means for distributing a microsphere carrying a sequencing template into a thermal cycling chamber. Autovalving means are used to ensure that only one microsphere will flow into one thermal cycling chamber. Extension means, including the thermal cycling chamber, produce thermal cycling extension fragments from a microsphere carrying a sequencing template. Integrated purification chamber means are used for capturing, purifying and concentrating the extension fragments. Component separation means are used to analyze the extension fragments.

Other implementations of the invention may include one or more of the following features. The extension means is a Sanger extension means including a plurality of thermal cycling chambers. The autovalving means includes an autovalve at an exit port of the thermal cycling chambers. Purification chamber means includes purification chambers connected to the thermal cycling chambers. The component separation means is a capillary array electrophoresis means including a plurality of microchannels connected to the purification chambers. The sequencing template is a DNA or RNA sequencing template.

In a further aspect, the invention is directed to a microfabricated apparatus including a thermal cycling chamber. The thermal cycling chamber is configured to receive a microsphere carrying a clonal template. The chamber has an inlet port and an outlet port wherein the outlet port includes a constriction that is configured to trap a microsphere in the chamber and to substantially block further flow into the thermal cycling chamber.

Various implementations of the invention may include one or more of the following features. The shape of the constriction is substantially circular or semicircular. A first value is located in an inlet channel in fluid communication with the inlet port and a second valve is located in an outlet channel in fluid communication with the outlet port. In operation, the second valve is closed before the first valve to move a microsphere out of the constriction and into a main body portion of the chamber before thermal cycling. A purification chamber is in fluid communication with the outlet port of the thermal cycling chamber and an outlet port of the purification chamber is in fluid communication with a component separation apparatus.

In yet another aspect, the invention features a system for performing sequencing. The system includes means for shearing DNA or RNA into fragments and means for ligating the fragments to form a mixture of desired circular and contaminating linear products. The system further includes means for selectively removing the contaminating linear products and means for generating microspheres carrying multiple clonal copies of a single sequencing template. The system also includes means for selecting which microspheres have a sequencing template and microfluidic distribution channel means for distributing a selected microsphere with a sequencing template into a thermal cycling chamber. Additionally, the system includes means for ensuring that statistically only one microsphere will flow into one thermal cycling chamber. The system also includes extension means, including the thermal cycling chambers, for producing thermal cycling extension fragments from the microspheres carrying multiple copies of the sequencing template. Purification chamber means for capturing, purifying and concentrating the extension fragments, and component separation means for analyzing the extension fragments are also part of the system.

Other implementations of the invention may include one or more of the following features. The ensuring means is at least one of an autovalve in the thermal cycling chamber, an optical detector, and a timing mechanism. The optical detector is an optical scanner that detects light scattered from a microsphere. The timing mechanism includes a pneumatic input located adjacent to an inlet of a thermal cycling chamber.

In a further aspect, the invention features a system for performing DNA sequencing. The system includes means for shearing DNA into DNA fragments and means for ligating the DNA fragments to form a mixture of desired circular and contaminating linear products. The system also includes means for exonuclease degradation for selectively removing the contaminating linear products and emulsion PCR reaction means for generating microspheres carrying multiple clonal copies of a single DNA sequencing template. Additionally, the system includes fluorescent activated cell sorting (FACS) means for selecting which microspheres have a DNA sequencing template. Microfluidic distribution channel means are used to distribute a selected microsphere with a DNA sequencing template into a thermal cycling chamber. Autovalving means are used to ensure that statistically only one microsphere will flow into one thermal cycling chamber. Sanger extension means, including the thermal cycling chambers, are used to produce thermal cycling extension fragments from the microspheres carrying multiple copies of the DNA sequencing template. Integrated purification chamber means are used to capture, purify and concentrate the extension fragments, and capillary array electrophoresis means are used to analyze the extension fragments.

In still another aspect, the invention is directed to a process for performing sequencing. The process includes shearing DNA or RNA into fragments, ligating the fragments to form a mixture of desired circular and contaminating linear products, and selectively removing the contaminated linear products. The process further includes generating microreactor elements carrying multiple clonal copies of a sequencing template, selecting which microreactor elements have a sequencing template, and distributing the microreactor elements with the sequencing template into thermal cycling chambers. Thermal cycling extension fragments are produced from the microreactor elements carrying the multiple copies of the sequencing template. The extension fragments are captured, concentrated, and analyzed.

Various implementations of the invention may include one or more of the following features. The microreactor element includes a microcarrier element which carries the multiple copies of the clonal sequencing template. The microreactor element is a bolus or a microemulsion droplet. The microreactor element includes a microsphere carrying the multiple copies of the clonal sequencing template. The distributing step is done such that only one microreactor element will pass into one thermal cycling chamber. An autovalve is used at an exit port of the thermal cycling chambers to ensure that only one microreactor element will flow into one thermal cycling chamber. The generating step includes generating multiple clonal copies of a sequencing template by emulsion PCR reactions or by a flow through PCR process. The selecting step is FACS.

In yet another aspect, the invention features a process for performing DNA sequencing. The process includes shearing DNA into DNA fragments, ligating the DNA fragments to form a mixture of desired circular and contaminating linear products, and selectively removing the contaminating linear products by exonuclease degradation. Microspheres carrying multiple clonal copies of a DNA sequencing template are generated by emulsion PCR reactions. The microspheres that have a DNA sequencing template are detected by FACS. The microspheres with the DNA sequencing template are distributed into thermal cycling chambers. An autovalve at an exit port of a thermal cycling chamber is used to ensure that statistically only one microsphere will flow into one thermal cycling chamber. Thermal cycling extension fragments are produced from the microspheres carrying multiple copies of the DNA sequencing template. The extension fragments are captured, purified, concentrated and analyzed.

Various implementations of the invention may include one or more of the following features. The capturing step uses an oligonucleotide capture matrix.

In still another aspect, the invention features a method for sequencing. The method includes receiving a microsphere carrying a clonal template at an inlet port of a thermal cycling chamber and using a constriction at an outlet port of the chamber to trap the microsphere in the chamber and substantially block further flow into the chamber.

In a further aspect, the invention features a method for analysis including producing a microsphere carrying a sequencing template. The microsphere is located in a thermal cycling chamber by use of a constriction at an outlet port in the chamber such that further flow into the chamber is substantially blocked.

Other implementations of the invention may include one or more of the following features. A first valve is located at an inlet port of the thermal cycling chamber and a second valve is located at an outlet port of the thermal cycling chamber such that the second valve may be closed before the first valve. As such, a microsphere is moved out of the constriction and into a main body portion of the thermal cycling chamber before thermal cycling.

The invention can include one or more of the following advantages. The laborious bacterial manipulations required by shotgun genome sequencing are replaced with easily automated and integrated in vitro steps. As such, millions of manual or robotic colony picking operations are eliminated. All fluidic and temperature control structures necessary to produce, purify, and separate sequencing extension fragments are integrated on a microfabricated device. Significant cost, time, and space savings can be achieved. Other genetic analysis techniques can be performed.

These and other features and advantages of the present invention will be presented in more detail in the following specification of the invention and the accompanying figures, which illustrate, by way of example, the principles of the invention.

BRIEF DESCRIPTION OF DRAWINGS

The invention may best be understood by reference to the following description taken in conjunction with the accompanying drawings that illustrate specific embodiments of the present invention.

DETAILED DESCRIPTION

Reference will now be made in detail to some specific embodiments of the present invention including the best modes contemplated by the inventor for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. The present invention may be practiced without some or all of these specific details. In other instances, well known process operations have not been described in detail in order not to unnecessarily obscure the present invention.

Furthermore, techniques and mechanisms of the present invention will sometimes be described in singular form for clarity. However, it should be noted that some embodiments can include multiple iterations of a technique or multiple applications of a mechanism unless noted otherwise.

The system and method of the present invention will be described in connection with DNA sequencing. However, the system and method may also be used for RNA sequencing. Additionally, the system and method may be used for other genetic analysis of DNA or RNA.

The system and method of the present invention uses microreactor elements such as a microemulsion droplet or a bolus which, in some embodiments, include a microcarrier element such as a microsphere or bead. The microcarrier element, contained within a bolus or a microemulsion droplet, is useful in capturing DNA or RNA products; that is, amplified DNA or RNA can be chemically linked to the microcarrier element. Alternatively, the amplified DNA or RNA may be carried by a microreactor element without the use of a microcarrier element. For instance, a PCR reaction may be done in a bolus or a microemulsion droplet, and then the resulting bolui or microemulsion droplets may be routed to the next step of the process.

Figure 1:
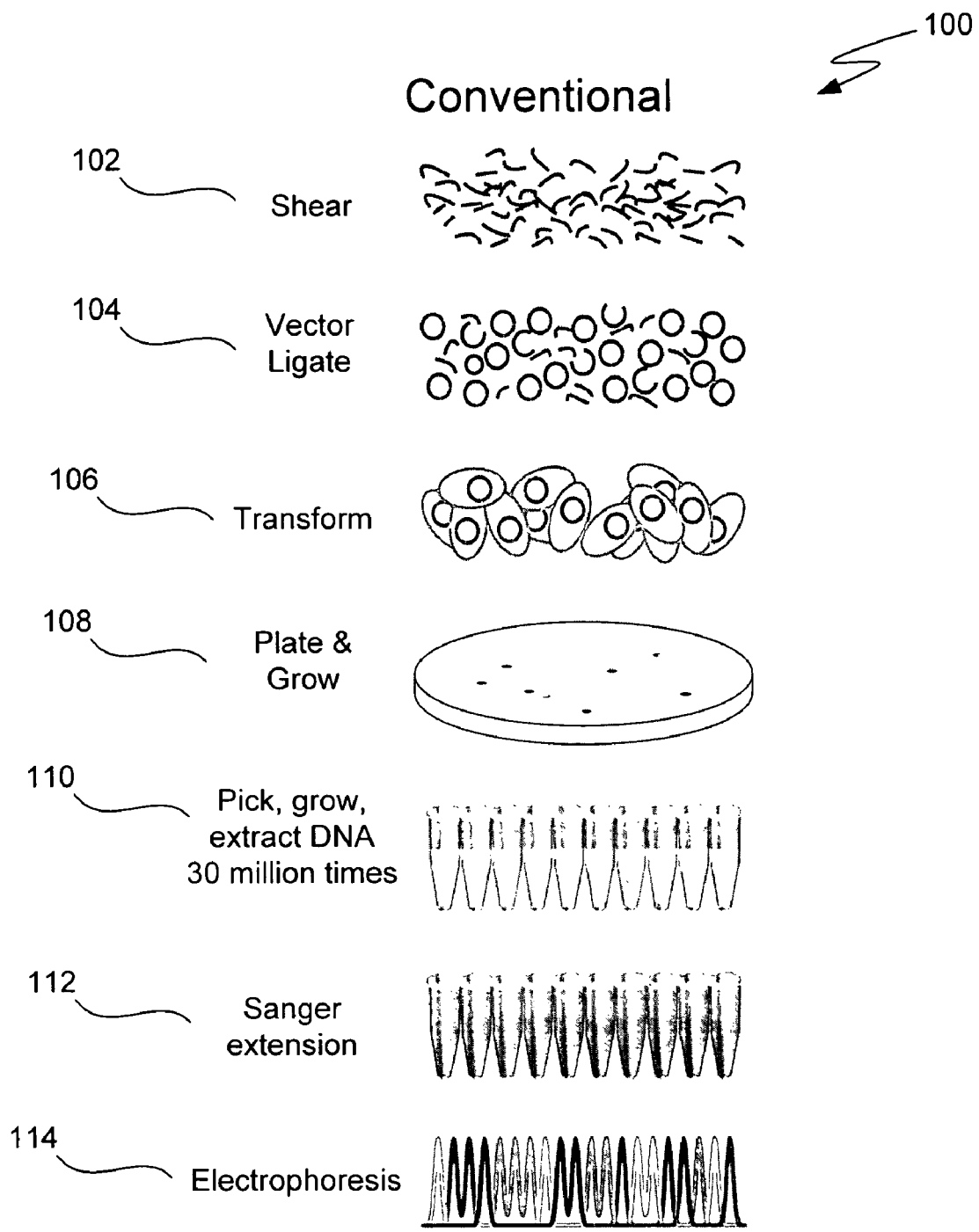
FIG. 1 is a diagrammatic representation of the steps involved in a conventional genome-scale sequencing operation.
Figure 2:
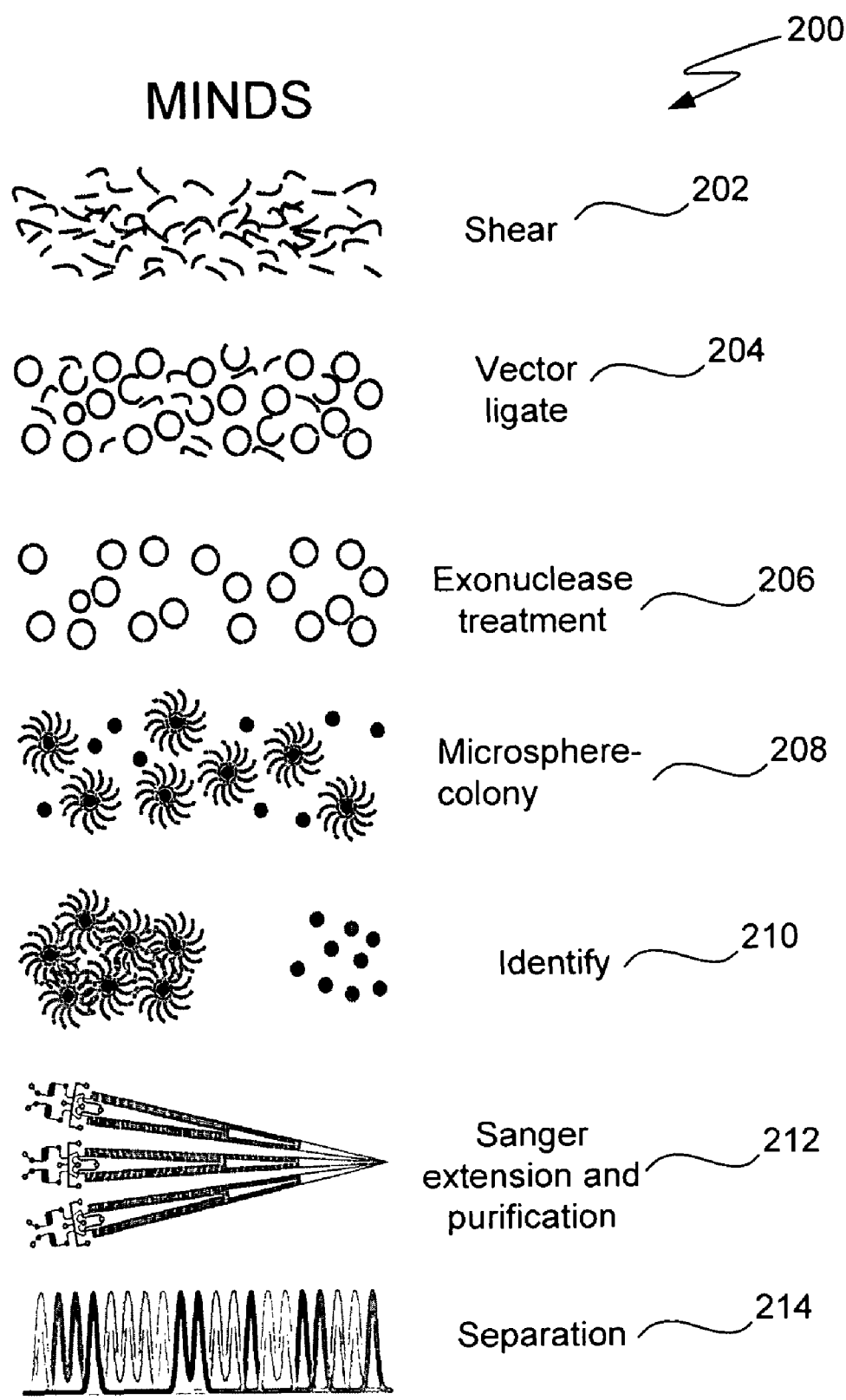
FIG. 2 is a diagrammatic representation of the steps involved in a genome sequencing process in accordance with the present invention.

A microfabricated integrated DNA analysis system (MINDS) of the present invention provides a system and method that are readily compatible with microfluidic sample component separation devices. As shown by FIG. 2, the MINDS process 200, in one embodiment, begins with the shearing of DNA into DNA fragments (step 202). The fragments are then ligated to form a mixture of desired circular and contaminating linear products (step 204). The contaminating linear products are then selectively removed, for instance, by exonuclease degradation (step 206). A colony of microspheres carrying multiple clonal copies of a DNA sequencing template is next formed (step 208). The colony may be generated, for example, by emulsion PCR reactions. The microspheres having a DNA sequencing template are then identified (step 210). The microspheres may be identified by a fluorescence activated cell sorting (FACS) technique. Only one such run is required, and it may take 6 hours or less to complete. The microspheres with the DNA sequencing templates are then distributed into thermal cycling or sequencing reaction chambers where extension fragments are produced; thereafter, the fragments are purified and concentrated (step 212). The extension fragment are then analyzed by a sample component separation apparatus, for example, a CE device (step 214).

The MINDS method, process, and apparatus, in one embodiment, comprises a microfabricated structure on which thermal cycling, affinity capture, sample purification, and capillary array electrophoresis (CAE) components are integrated. As will be discussed, such a system includes a microfluidic distribution channel to distribute microspheres carrying multiple copies of a sequencing template into a plurality of thermal cycling or sequencing reaction chambers. An autovalve may be located at an exit port of the thermal cycling chambers to ensure that only one microsphere will flow into each chamber wherein thermal cycling extension fragments are produced from the microsphere. Purification chambers are connected to the thermal cycling chambers to capture, purify, and concentrate the extension fragments. Microfabricated CE separation channels are connected to the purification chambers to analyze the extension fragments.

The present invention eliminates the laborious, expensive, and time consuming in vivo cloning, selection, colony isolation, and amplification steps of conventional sequencing. Instead, these steps are replaced with readily miniaturized and automated in vitro steps.

Microspheres are ideal carriers, providing flexible control over size, surface, fluorescent, and magnetic properties. Miniaturization of a sequencing reaction chamber through microfabrication and the concomitant reduction in reagent volume makes possible the use of a single, clonal microsphere as a carrier for sufficient DNA sequencing template. This enables the use of a matched process flow that permits selection, amplification and sorting of clonal templates for direct integration with a nanoliter extension, clean-up and sequencing process.

Figure 3:
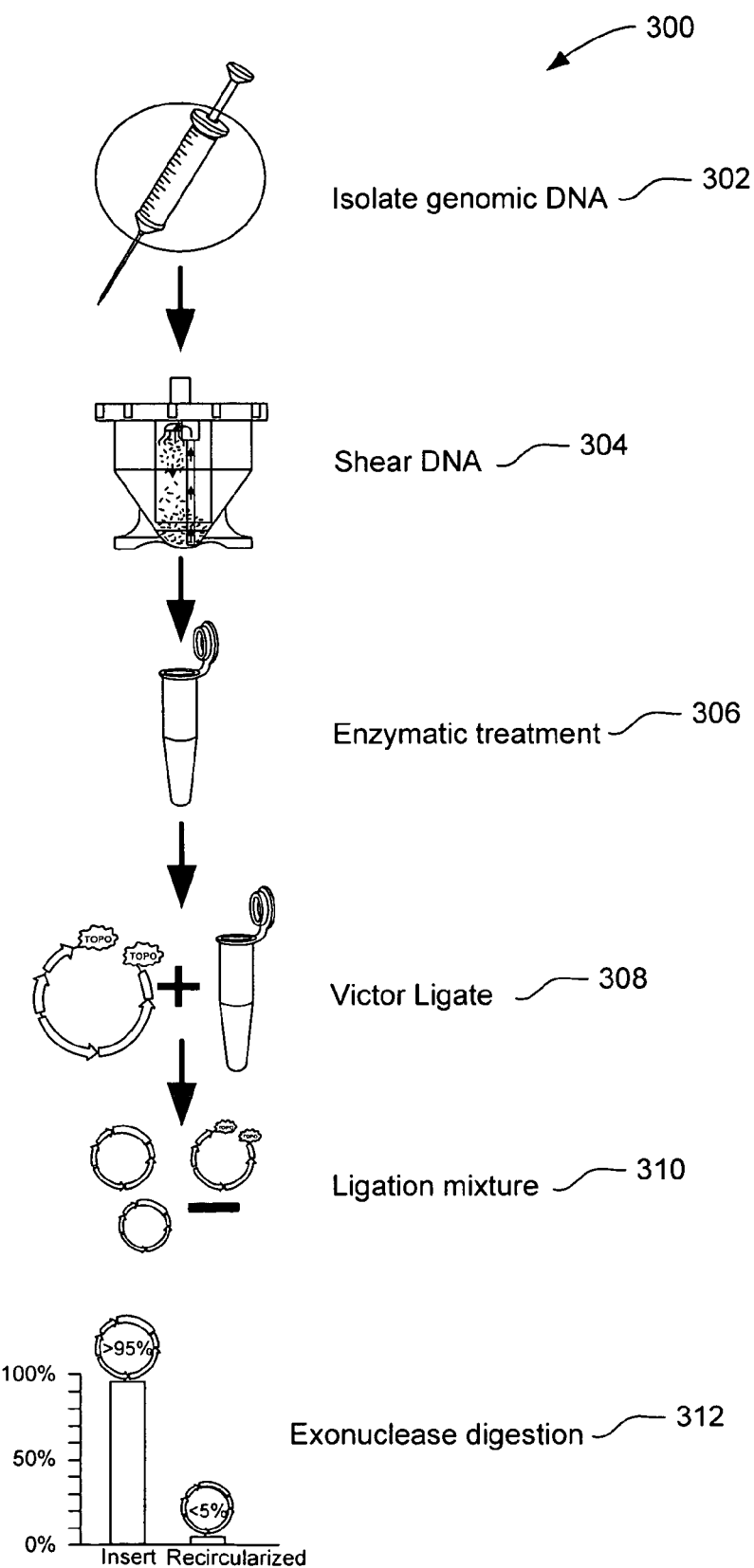
FIG. 3 is a diagrammatic representation of a cloning process that may be used with the present invention.

FIG. 3 provides an overview of a cloning process 300 that may be used with the MINDS. The process includes library creation and selection. In one embodiment, genomic DNA is isolated from whole blood and then sheared in a nebulizer generating DNA fragments (steps 302 and 304). The DNA fragments are then subjected to an enzymatic treatment to yield blunt-end DNA (step 306). Processed fragments are ligated into a vector yielding a mixture of desired circular and contaminating linear products (steps 308 and 310). Exonuclease degradation then selectively removes the insert and vector, the contaminating linear products, from the ligation product so that greater than about 95% of the remaining vectors contain inserts, the desired circular products (step 312).

The first five steps of the cloning process 300 (steps 302-310) follow standard library creation procedures. More specifically, Invitrogen (Carlsbad, Calif.) supplies a TOPO Subcloning Kit (#K7000-01) which is capable of generating a 1 to 6 Kb insert genomic shotgun library in two hours. The subcloning kit requires about 20 micrograms (µg) of genomic DNA that can be obtained from 1 mL of whole blood using Qiagen's (Oslo, Norway) Blood & Cell Culture DNA Mini Kit (#13323). The DNA is sheared in a nebulizer generating 1-6 Kb DNA fragments. The fragments are then subjected to an enzymatic treatment with T4 DNA and Klenow polymerases and calf intestinal phosphatase (CIP) to yield dephosphorylated blunt-end DNA. Processed fragments are next ligated into Invitrogen's pCR 4 Blunt-TOPO vector. Use of covalently linked vaccinia virus topoisomerase I to the cloning vector results in rapid and efficient ligation (a 5 minute room temperature ligation yields greater than 95% transformants) and permits dephosphorylation of the inserts prior to ligation thereby preventing chimeric clone formation.

The final step in canonical library creation (step 312), which has been modified to be compatible with the in vitro MINDS process, is bacterial transformation and antibiotic selection. Exonuclease degradation selectively removes insert and vector from the desired ligation product. Lambda exonuclease (New England BioLabs #M0262S) can be used for this step as it degrades 5'-phosphorylated and non-phosphorylated double-stranded DNA but is unable to initiate DNA digestion at the nicks present in the vector after ligation. Assuming a pessimistic 1% recovery of the starting genomic DNA, the resulting library contains greater than 6,000 fold molecular excess needed for 10× sequence coverage, though this excess is reduced through dilution in the single-molecule PCR amplification step described later.

A gel separation and band purification step can be performed after DNA shearing (step 304) if strict control over insert size is required for paired-end whole-genome de novo sequencing. Alternatively, insert size can be restricted using limiting extension times during PCR amplification or flow cytometric selection of microspheres within a narrow fluorescence intensity range. Labeling microsphere-clones with an intercalating dye, such as thiazole orange (TO), will yield a fluorescent signal proportional to amplicon size. Since flow cytometry is a step in the MINDS process, this is an appealing size-selection method that also eliminates the >5% recircularized vectors with the only drawback being reduced yield.

The vector used in the subcloning kit may be optimized for sequencing with the T7 and T3 priming sites 33 bp (base pairs) away from the insertion site. Since the MINDS vector is free from biological constraints, the sequencing priming sites can be moved closer to the insert site and the pUC ori, fl ori, lacZ, and antibiotic resistance genes can be removed. Optimized acrydite capture sequences and homo-PCR priming sites can be inserted for improved sample clean-up and reduced primer-dimer formation.

Sequencing in the MINDS process may use clonal template DNA attached to individual microspheres or beads. The clonal attachment is accomplished by linking one of the primers covalently to a microsphere.

Clonal isolation of 1,000 to 100,000 DNA molecules through single-molecule amplification (for example microemulsion polonies) or combinatorial hybridization approaches has been demonstrated. See, Mitra, R. D., et al., "Digital genotyping and haplotyping with plymearase colonies", *Proceedings of the National Academy of Sciences of the United States of America*, 2003, 100(10): p. 5926-5931; Dressman, D., et al., "Transforming single DNA molecules into fluorescent magnetic particles for detection and enumeration of genetic variations", *Proceedings of the National Academy of Sciences of the United States of America*, 2003, 100(15): p. 8817-8822; and Brenner, S., et al., "Gene expression and analysis by massively parallel signature sequencing (MPSS) on microbead arrays", *Nature Biotechnology*, 2000, 18(6): p. 630-634; each of which is hereby incorporated by reference. Conventional microchip sequencing requires approximately 1 billion template DNA molecules per reaction. Twenty billion extension fragments have been generated after 20× linear Sanger-sequencing amplification, representing a 20-fold excess for high signal-to-noise (S/N) detection using a confocal radial scanner (1 million fragments per band×1,000 bands=1 billion molecules). This excess is necessary because a cross-injection process requires streaming extension fragments across the separation column until an equimolar mixture is obtained at the intersection and then injecting about 5% of the total sample. An affinity capture direct-injection strategy discussed below eliminates the 20-fold excess requiring only 50 million initial template copies.

CPG Biotech (Lincoln Park, N.J.) produces a 5 micron (μm) controlled pore glass paramagnetic microsphere with a long chain alkylamine linker for covalent attachment to an amine modified primer that can consistently bind 80 million DNA molecules. Starting from a single DNA molecule, 30 cycles of PCR has a theoretical gain of 1 billion. In practice, the gain is lower due to less than 100% efficiency for each cycle, reduced enzyme activity in later cycles, and limiting reagents in pL scale reactions. To generate clonal microspheres, a single DNA molecule and a single primer-coupled microsphere must be placed in a PCR reactor. Efficient single-molecule PCR requires extremely small volume reactors (1-10 pL) to increase the effective concentration of a single DNA molecule. Approximately 30 million microsphere clones are needed to sequence a human-size genome. High-throughput combination of a single microsphere and DNA molecule in a chamber is possible using statistically dilute microemulsion solutions. If the DNA molecules and microspheres are each diluted such that one species is present in 10 times the reactor volume, there is a high probability (greater than 99%) of concurrence in 1% of the reactors. Because 99% of the reactors are non-productive, 100-fold more reactions (3 billion) are required to generate 30 million microsphere clones.

Two possible approaches for generating large numbers of small volume reactions are microfabricated PCR devices and emulsion PCR. PCR devices, however, require thousands of runs to achieve the required 3 billion reactions. Emulsion PCR, on the other hand, has the ability to thermally cycle millions to billions of separate compartments in a single tube using a conventional thermal cycler. Clonal PCR amplicons attached to magnetic particles using emulsion PCR have been produced. On average, each microsphere contained greater than 10,000 250 bp amplicons, a value below the theoretical maximum of 600,000 amplicons based on the available nucleoside triphosphates in each 5 μm diameter compartment. Fifteen micron microemulsion PCR compartments have been demonstrated in which the maximum number of 1,000 bp amplicons is 5 million—a value ten times less than the minimum required 50 million initial template copies. This problem may be solved in a variety of ways:

First, additional microemulsion PCR steps could be performed to increase the amount of DNA linked to the beads. Second, an additional non-reagent-limited amplification step may be necessary after the fluorescence flow cytometry step. Secondary PCR amplification can be performed in an on-chip, dual-use thermal cycling chamber in which paramagnetic microspheres are routed to individual reactors and magnetically retained. Fresh PCR mix is passed into the chambers and thermal cycled 15× to saturate each microsphere to the maximum of 80 million templates. In this case, the magnetic field is maintained as Sanger-sequencing reaction mix is washed into the chambers followed by solid-phase sequencing. Finally, the S/N of the scanner may be improved up to 10-fold enabling sequencing of about a 10-fold lower template than calculated above.

Approximately 15 million 15 μm diameter compartments may be created in a 25 μL aqueous phase, 75 μL oil phase emulsion. Three billion compartments are required to generate 30 million coincident single DNA molecule and microsphere events. Thus, approximately two 100 L 96-well plate reactions are required. When the reactions are complete, 30 million microsphere clones must be separated from a background of 300 million un-labeled microspheres.

As noted, the beads having sequencing templates may be identified by FACS. A system that may be used is the BD FACS ArrayBioanalyzer System, available from BD Biosciences, San Jose, Calif. The BD FACSArray flow cytometer can process up to 15,000 events per second, enabling the isolation of all clones needed for 10× coverage of a 3 billion base genome in less than 6 hours. The beads will be treated with an intercalation dye, such as TO, that is nonfluorescent until intercalated into double-stranded DNA. The fluorescence intensity of TO is linearly proportional to the amount of DNA allowing for easy differentiation between beads that have amplified DNA and those that do not.

Figures 4A, 4B:
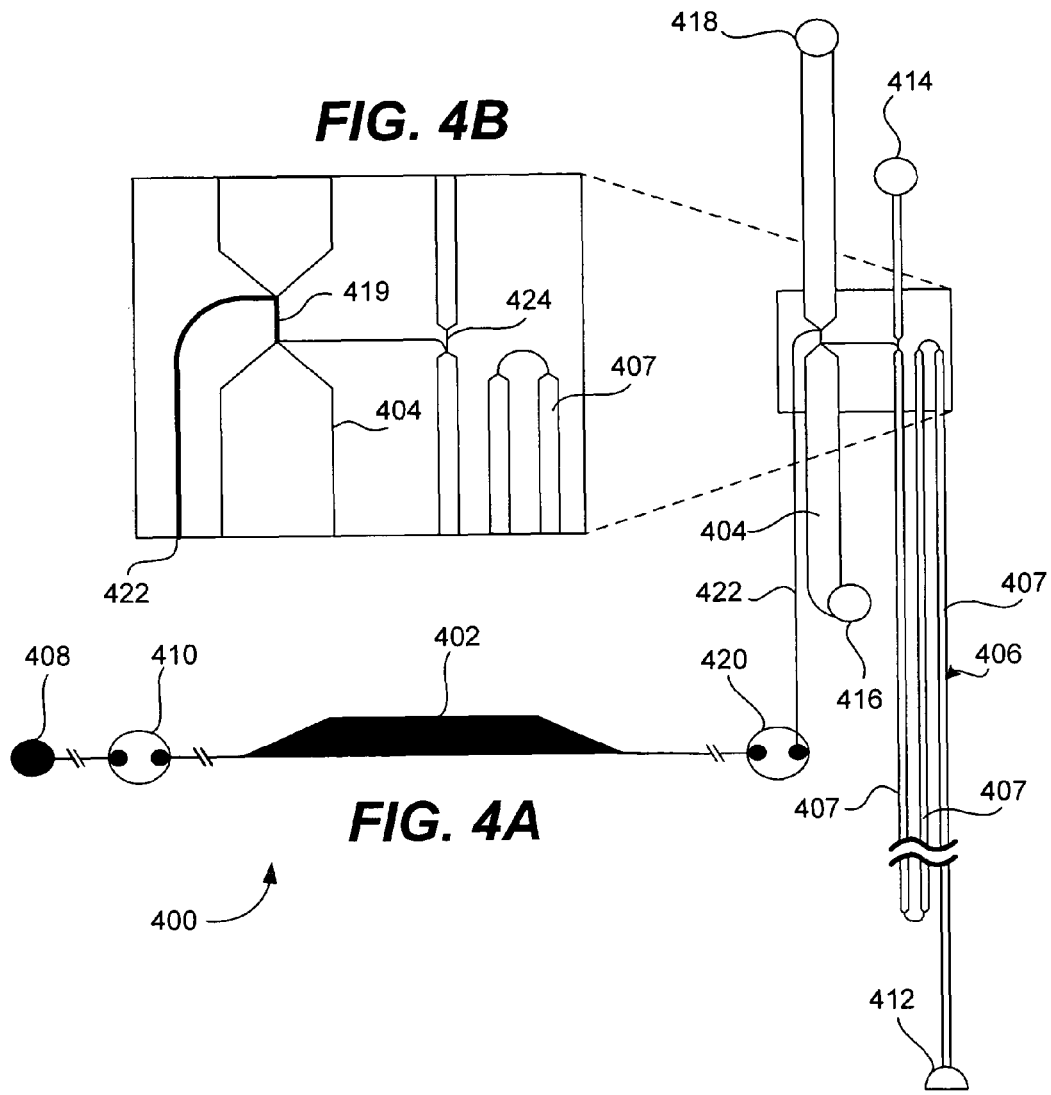
FIG. 4A is a diagrammatic representation of a single-channel microdevice in accordance with the present invention.
FIG. 4B is an enlarged view of a portion of the device of FIG. 4A.
Figure 4C:
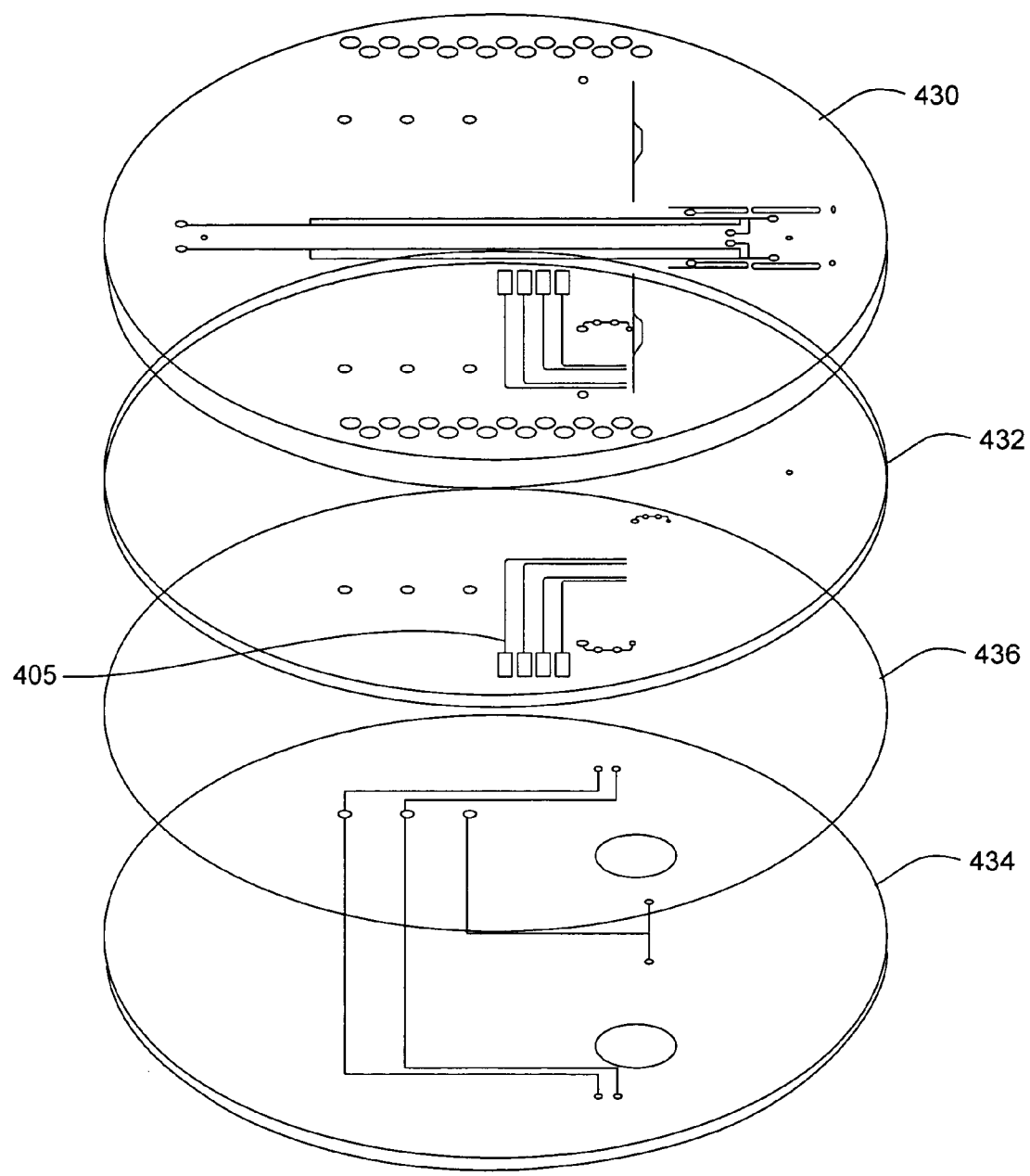
FIG. 4C is a diagrammatic exploded view of the single-channel microdevice.

A diagrammatic representation of a single-channel microdevice 400 in accordance with the present invention is shown in FIGS. 4A, 4B, and 4C. The device may be fabricated as a four layer glass-glass-PDMS (polydimethysiloxane)-glass sandwich that incorporates microfluidic valves, heaters, resistive temperature detectors (RTDs), and all reaction, capture and clean-up, and CE structures. The device, in another configuration, may be fabricated as a glass-PDMS-glass-glass stack. A four layer microfabricated system including valves, heaters, RTDs, chambers, and CE structures is described in U.S. patent application Ser. No. 10/750,533, filed Dec. 29, 2003, entitled "Fluid Control Structures In Microfluidic Devices", assigned to the Assignee of the subject application, and which is hereby incorporated by reference.

The microdevice 400 is capable of performing all downstream steps in the MINDS process including extension fragment production, reaction clean-up, and extension fragment separation (steps 212 and 214 of FIG. 2). The device 400 includes a thermal cycling or sequencing reaction chamber 402, a capture or purification chamber 404, and a CE system 406 including separation channels 407. As shown, these components of the device 400 are connected by various valves and channels. A heater (not shown), for example, a kapton heater, may be used to heat the contents of the thermal cycling chamber. The template of the chamber is monitored by RTDs 405.

As shown in FIG. 4C, the device 400 includes three glass layers, including a channel layer 430, a via layer 432, and a manifold layer 434. A PDMS membrane layer 436 is provided between the via layer 432 and the manifold layer 434. The top layer 430 contains the thermal cycling reactors, the capture chambers and the CE features. The second layer 432 incorporates the RTDs on the top surface of the glass wafer and etched features on the bottom to form the valves and pumps with the membrane layer 436 below. The last layer 434 includes the heater, and completes the valve and pump structures with pneumatic actuation lines and displacement chambers.

In one method of operation, a sequencing master mix is loaded from a port 408 of the device 400 through a microvalve 410 into the thermal cycling chamber 402. The volume of the chamber 402 may be approximately 250 nano-liters (nL). The separation channels of the CE system 406 are filled with linear polyacrylimide from a port 412 to a port 414. The CE system may be a 16-centimeter (cm) hyperturn system. An acrydite capture matrix is loaded from a port 416 to a port 418 to fill the capture chamber 404 and an intervening pinched chamber 419. After thermal cycling the chamber 402, extension fragments and residual reactants are electrokinetically driven through a valve 420 and a channel 422 into the capture chamber 404. The captured extension fragments are then electrophoretically washed and injected into a channel 424 for separation by the CE system 406.

Figure 5A:
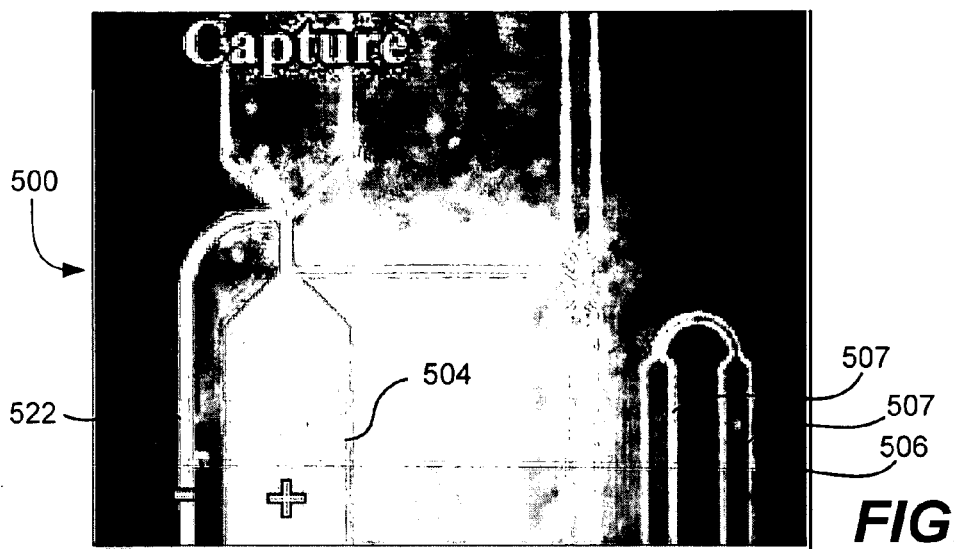
FIGS. 5A, 5B, and 5C are fluorescent images of a device in accordance with the present invention during capture, wash, and sample injection, respectively, of extension fragments.
Figure 5B:
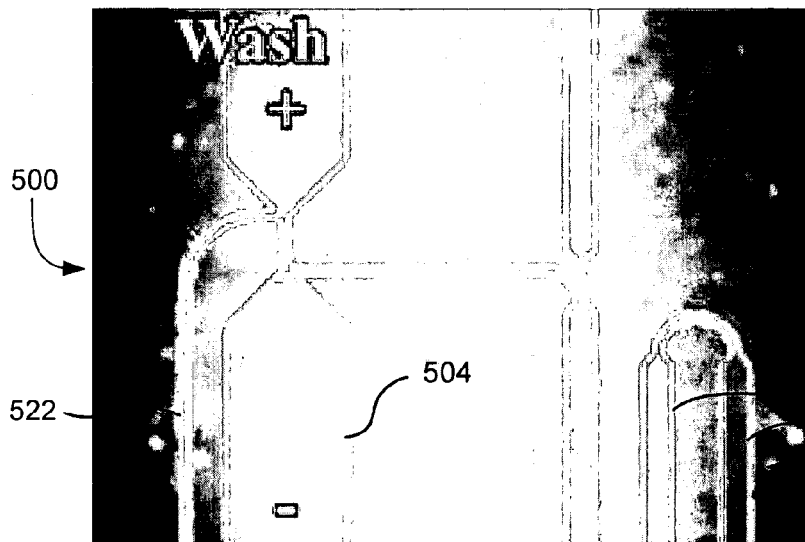
Figure 5C:
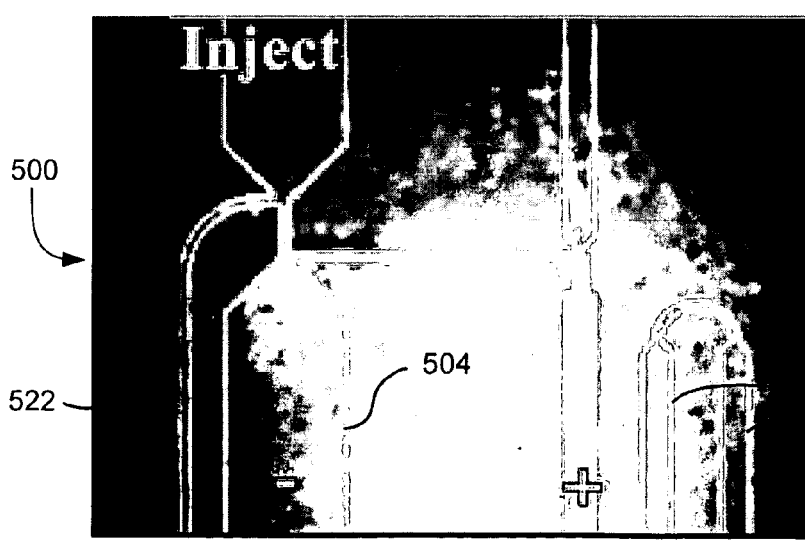

An advantage of this affinity capture, sample clean-up microdevice is that purified extension fragments may be retained in 1-10 nL at a concentration determined by the quantity of the acrydite monomer added during synthesis. FIGS. 5A, 5B, and 5C display fluorescence images (where relative applied potentials are indicated by "+" and "−") from the operation of a microdevice 500 like that of the device 400 where thermal cycling, capture, wash (purification), and concentration of a sample as well as separation were performed. Specifically, an acrydite capture matrix was synthesized in a 2-mL solution of 5% w/v acrylamide, 1×TTE (50 mM Tris, 50 mM TAPS free acid, 1 mM EDTA, pH=8.4), and 20 nmol of the methacrylate-modified oligo (5'-Acrydite-ACTGGC-CGTCGTTTTACAA-3' (SEQ. ID NO. 1), $T_M$=60.4° C., Operon Technologies, Emeryville, Calif.). The solution was sparged with argon for 2 hours prior to adding 0.015% w/v APS and TEMED to initiate polymerization. The polymerized capture matrix was then loaded into a capture chamber 504 using a 1 mL syringe. A polymer sequencing matrix (CEQ, Beckman Corp., Fullerton, Calif.) was loaded into a CE system 506 using a high-pressure gel loader. A C-track master mix was prepared containing 80 nM ET-primer, 1×C terminator mix (Amersham), and 4 nM PCR product and injected into a 250 nL thermal cycling chamber or reactor (not shown). Thermal cycling (35×, 94° C. 30 seconds, 45° C. 40 seconds, 70° C. 40 seconds) was performed on-chip using a LabVIEW program (National Instruments, Austin, Tex.).

Sequencing reaction clean-up was performed by first equilibrating the microdevice on a 50° C. heated stage for 30 seconds. Then, sample capture (FIG. 5A) was initiated by applying 2000 V to the capture chamber outlet (port 416 of FIG. 4A) while grounding the reactor inlet (port 408 of FIG. 4A). Thus, the sample containing extension fragments and residual nucleotides, primers, and salts was electrophoretically driven from the thermal cycling chamber through a channel 522 into the capture chamber 504. Extension fragments hybridize to the Acrydite matrix in the capture chamber while residual reactants pass through. When oligonucleotide capture was complete, the retained extension fragments were electrophoretically washed (FIG. 5B) for 30 seconds to remove excess primer and other contaminants still present in the capture chamber. After electrophoretic washing, the stage was ramped to 70° C. and equilibrated for 60 seconds to allow full denaturation of the product-matrix duplex. The denatured sample is directly injected into separation columns 507 of the CE apparatus 506 (FIG. 5C) by applying 2,500 V to the anode while grounding the capture chamber outlet. (Images have been processed to highlight channel structure and remove fluorescent surface contamination.)

Alternatively, a straight cross-injector and a 30-cm separation capillary could be used. This will improve resolution.

The microsphere-colony creation procedure and a single reactor microdevice can generate single-ended reads suitable for resequencing efforts. De novo whole-genome shotgun sequencing of complex genomes requires paired-end reads from short and long insert clones. Long-range PCR followed by fluorescent flow cytometry can be used on a subset of microspheres to selectively generate long-insert clones. Traditional paired-end sequencing requires procedural and microdevice modifications such that clonal DNA could be released from the microspheres and routed to separate forward and reverse sequencing reactors. An alternative strategy is to perform forward and reverse sequencing simultaneously on a subset of bases using an altered base labeling scheme. These paired-end reads generate long single or double-base reads suitable for anchoring four-base single-ended reads in the sequence assembly.

Figure 6A:
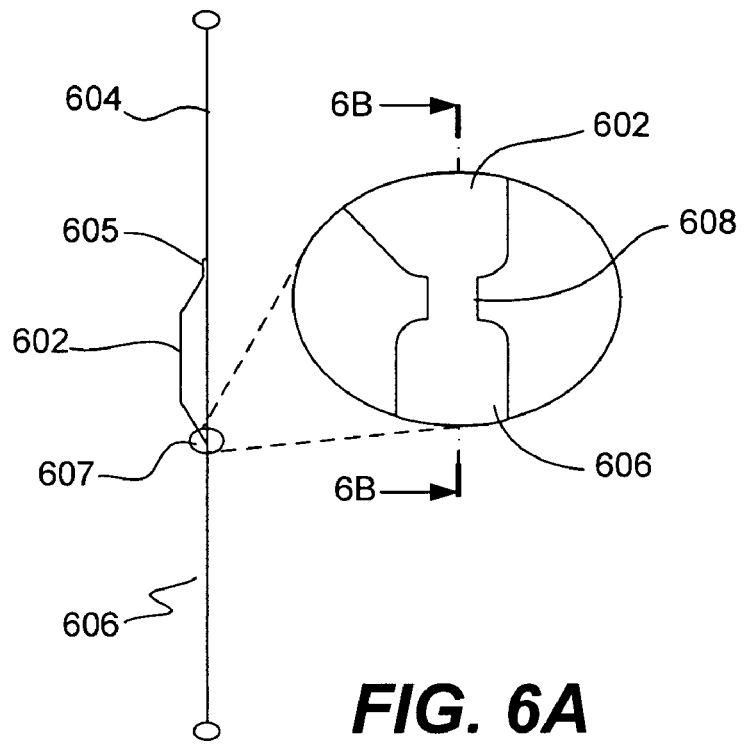
FIG. 6A is a diagrammatic representation of a sequencing reaction chamber of a device in accordance with the present invention, including an enlarged view of a portion of the reaction chamber.
Figure 6B:
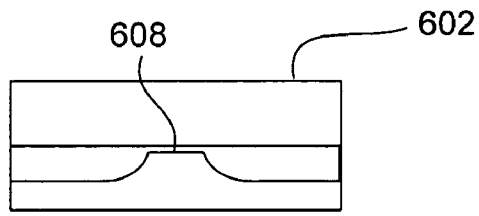
FIG. 6B is a view along line 6B-6B of FIG. 6A.
Figure 6C:
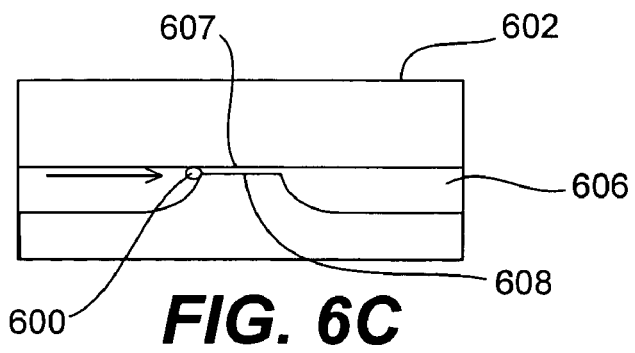
FIG. 6C is a diagrammatic representation of a constriction region of the reaction chamber of FIG. 6A that is used to trap beads carrying the DNA to be sequenced.

As illustrated in FIGS. 6A, 6B and 6C, a microsphere 600 is used to transfer a clonal template into a thermal cycling or sequencing reaction chamber 602 where sequencing reactions are performed. This process requires that one microsphere be introduced in each sequencing reaction chamber. Autovalving techniques for trapping an individual microsphere in a sequencing reaction chamber, without the need for individually actuated valves and sensing, are used for this purpose.

As shown, the reaction chamber 602 includes an introduction channel or arm 604 and an exit channel or arm 606. The introduction channel is in fluid communication with an inlet port 605 of the reaction chamber, while the exit channel is in fluid communication with an outlet port 607 of the reaction chamber. Self-valving is achieved by creating a constriction or constriction region 608 at the outlet end or port 607 of the reaction chamber. The constriction region is semicircular in shape.

The constriction will trap a microsphere before it exits the chamber. The trapped microsphere will produce a drop in the flow rate, thereby preventing any further microspheres from flowing into the chamber. The dilution of the microspheres will be chosen such that the probability that another microsphere flows into the reaction chamber before the first microsphere has blocked the chamber is below about 0.5%. If this statistical approach is unreliable or leads to low sorting rates, an on-chip sensor for bead light scattering can be used, and two valves in the sorting loop can be added to produce a more temporally uniform bead distribution.

Glass fabrication processes can be used to create the device shown in FIGS. 6A-6C. In one example, all features except the constriction were isotropically etched to a depth of 30 μm. The sample introduction and exit channels were set to 70 μm in width and 15 mm in length. The sequencing reaction chamber had a volume of 250 nL. After the basic fabrication process was completed for the channels and the reaction chamber, a second mask was used to fabricate the constriction. For this, a more viscous photoresist (SJR 5740, Shipley, Marlborough, Mass.) was spin-coated on a wafer at 2500 rpm for 35 seconds. This was followed by a soft bake at 70° C. for 7 minutes and 90° C. for 6 minutes. A higher viscosity photoresist gives more uniform coating on the featured wafer. The constriction pattern was transferred to the coated wafer using a contact printer. Alignment marks were used to align (±1 μm) the constriction with the already etched channels and chamber. After development, the amorphous silicon masking layer was removed via plasma etching, and the exposed glass was wet etched using 5:1BHF with an effective etch rate of 2 μm/hour for 1.5 hours. This gave a constriction depth or height of 3 μm. The constriction width was set to 8 μm and the length was set to 15 μm.

Testing of the self-valving concept was performed using 6 μm diameter, Streptavidin Coated Fluoresbrite YG Carboxylated Polystyrene microspheres (Polysciences Inc., Warrington, Pa.) suspended in a solution of 1× Tris (pH 8.0) and 1% Triton X-100 diluted to a final concentration of 1 microsphere/3 μL. Using the Poisson distribution, it was calculated that a 10× dilution of the reaction chamber volume will insure that the probability that another microsphere will enter the 250 nL chamber before the first microsphere blocks the constriction is below 0.5%.

A device like that shown in FIGS. 6A-6C was pre-filled with a solution of 1× Tris (pH 8.0) and 1% Triton X-100. The microsphere solution (6 μL) was pipetted into an inlet access hole. A vacuum line was used to draw the beads through the chamber. The pressure drop increased from −60 kPa to −70 kPa when a microsphere was trapped at the constriction, and blockage occurred within the first 60 seconds. The experiment was continued for 12 minutes and no other microsphere was observed to enter the chamber.

Figure 7A:
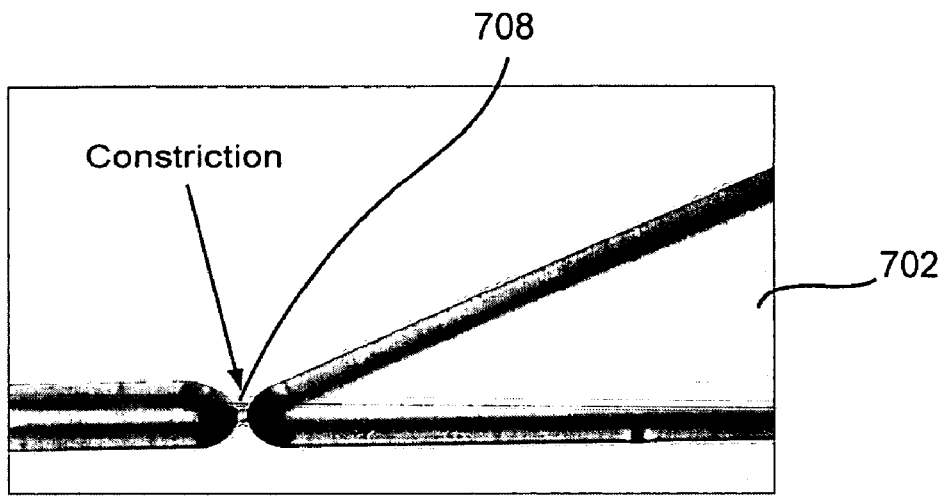
FIG. 7A is a bright field image of a constriction region of an empty sequencing reaction chamber.
Figure 7B:
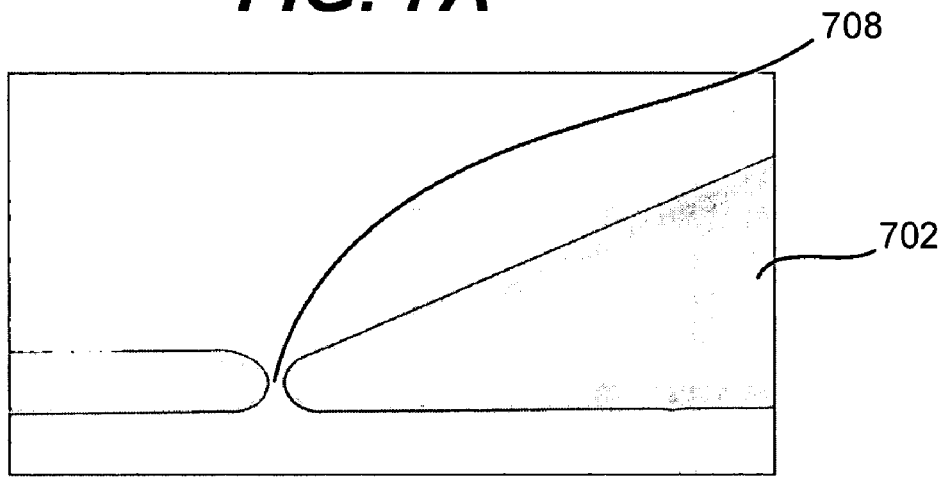
FIG. 7B is a bright field image of a constriction region of a sequencing reaction chamber filled with solution but with no microsphere at the constriction region.
Figure 7C:
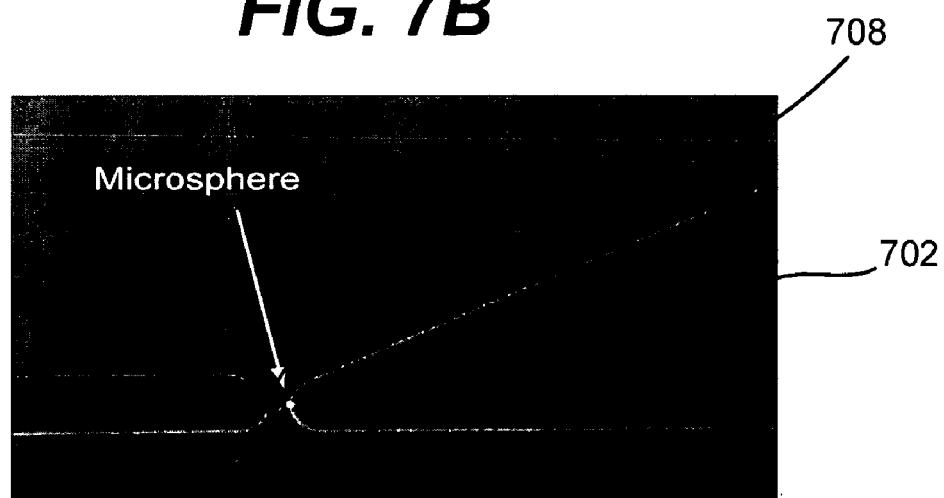
FIG. 7C is a dark field image of a microsphere located at a constriction region of a sequencing reaction chamber.

FIGS. 7A and 7B show bright field images of a constriction region 708 of a thermal cycling chamber 702 at 20× magnification when empty and with solution (but no microsphere), respectively. FIG. 7C shows a dark field image of the thermal cycling chamber 702 with a fluorescent microsphere 700 trapped at the constriction 708 and acting as a valve. The experiments were performed for microspheres of approximately 6 μm diameter. The concept is easily scalable to larger microspheres to increase the number of templates in the reactor. Also, smaller microsphere could be used. The microspheres, in particular, may be between about 1 and 100 μm in diameter. In one embodiment, they are about 10 μm in diameter.

Figure 8A:
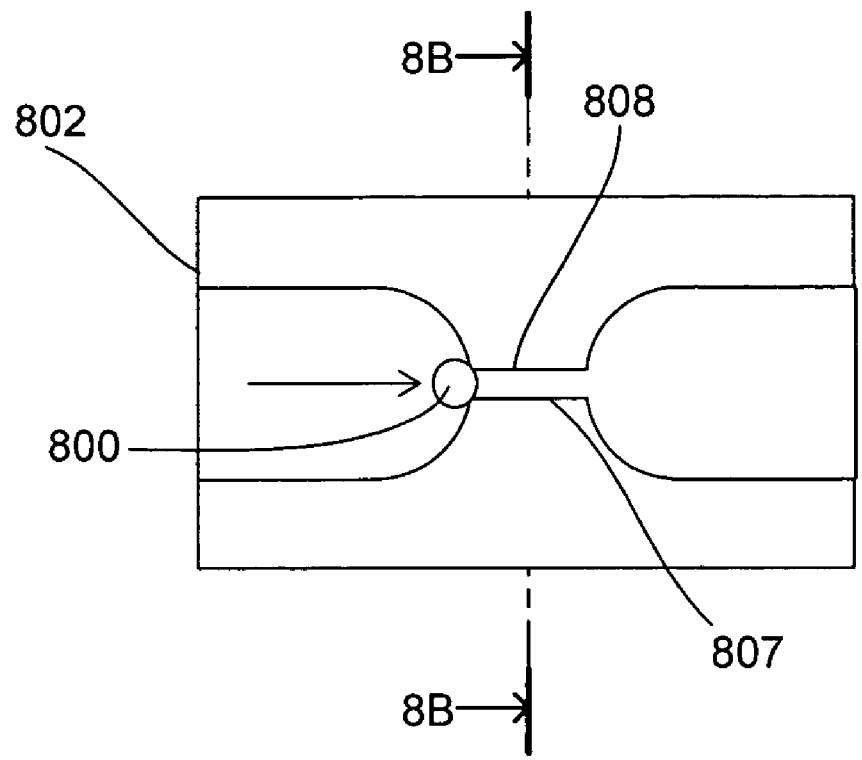
FIG. 8A is a diagrammatic representation of an alternate embodiment of a constriction region of a sequencing reaction chamber designed for bead capture.
Figure 8B:
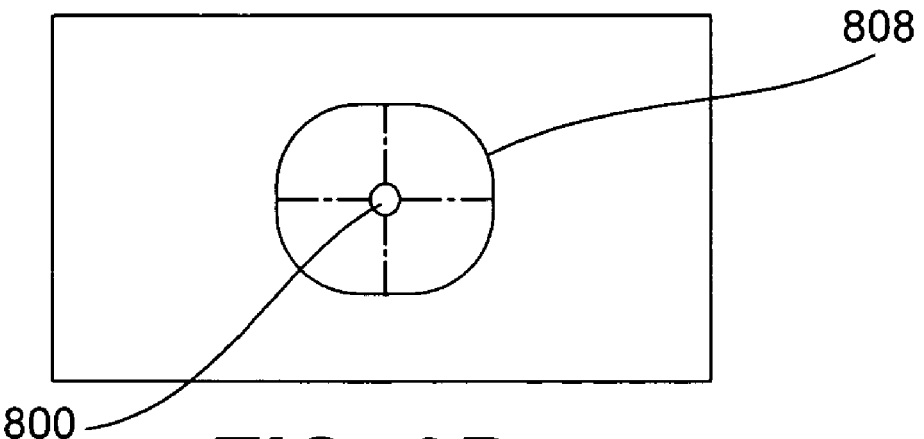
FIG. 8B is a view along line 8B-8B of FIG. 8A.

An alternative autovalving embodiment, which will result in complete flow blockage, is presented in FIGS. 8A and 8B. Here, a reaction chamber 802 has a near circular constriction or constriction region 808 formed at a chamber outlet port 807. The chamber and the constriction will be double-etched; that is, they will be etched on both of two joined glass surfaces. This will produce a near circular constriction, as opposed to a semicircular constriction of the embodiment of FIGS. 6A-6C. This will provide better valving for trapping a microsphere 800.

As discussed, valves will be incorporated on either side of a sequencing reaction or thermal cycling chamber 402 (see FIGS. 4A and 4B). Once a microsphere has been trapped at the constriction, it needs to be pushed back into the chamber for thermal cycling so that there is good accessibility of the clonal templates to the polymerase, primers, dNTPs and ddNTPs. By closing the valve 420 at the outlet of the chamber before closing the inlet valve 410, the microsphere will be pushed back into the chamber as a result of the finite dead volume of the valves. This principle is easily scaled to an array system by actuating the inlet and outlet valves in parallel.

Figure 9A:
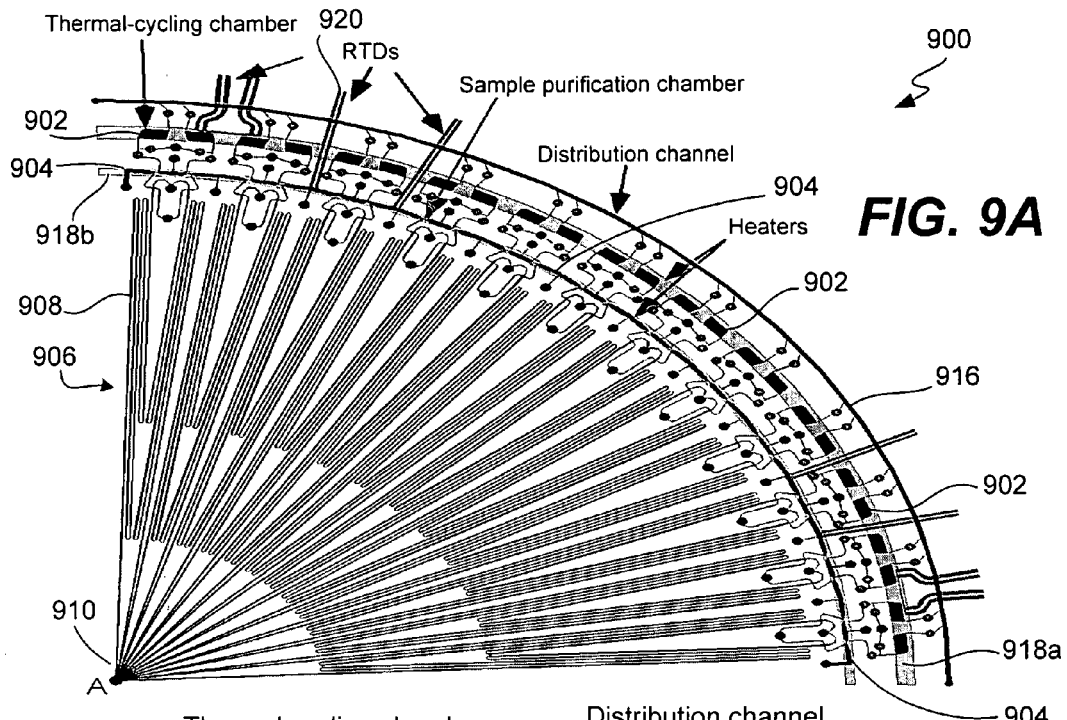
FIG. 9A is a diagrammatic representation of one quadrant of an integrated sequencing array system.
Figure 9B:
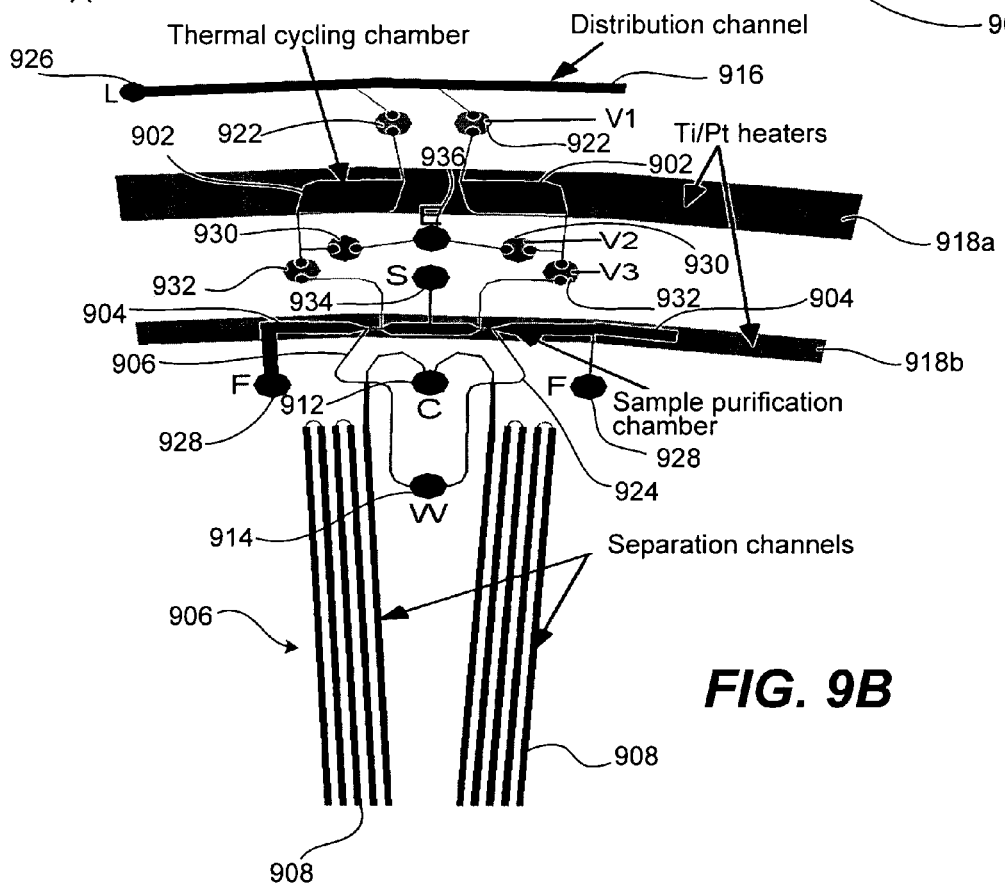
FIG. 9B is an enlarged view of a portion of the system of FIG. 9A.

To realize a high-throughput and fully integrated system for DNA analysis, a microfabricated array of integrated analyzers that incorporate thermal cycling chambers, purification chambers as well as separation channels for CE analysis of the sequencing fragments is provided. A schematic of such a system 900 is shown in FIGS. 9A and 9B. This system extends the single channel device of FIGS. 4A-4C to an array structure that is able to perform highly parallel analyses.

According to various embodiments, the system 900 includes multiple thermal cycling chambers 902 and associated sample purification or capture chambers 904 arranged about a circular axis to form a radially parallel system. The thermal cycling chambers and the sample purification chambers are all integrated with a CE analyzer system 906 including separation channels or microchannels 908. The CE analyzer has a common central anode (A) 910, a cathode reservoir (C) 912, and a waste reservoir (W) 914. The cathode and anode reservoirs are associated with adjacent sets of separation channels 908. The microchannels 908 are connected to the anode 910 for detection using a rotary confocal fluorescence scanner of the type discussed in the article entitled: "High-throughput genetic analysis using microfabricated 96-sample capillary array electrophoresis microplates", Peter C. Simpson, et al., *Proc. Natl. Acad. Sci. USA*, Vol. 95, pp. 2256-2261, March 1998, which is hereby incorporated by reference.

The system 900 further includes a distribution channel 916, integrated heaters 918a and 918b, and RTDs 920. The heaters 918a and 918b address the thermal cycling chambers and purification chambers, respectively, in parallel. As such, the use of simple ring heaters to drive the thermal cycling and sample purification reactions is more than adequate.

The temperature of these reactions are monitored by the RTDs. In one embodiment, four-equally spaced RTDs are integrated on the substrate to provide precise temperature sensing across the heater 918a for optimal thermal cycling performance. Similarly, four-equally spaced RTDs may be used to monitor the temperature of the heater 918b.

The system 900 also includes an array of integrated valves and ports for controlling the system flow process. The valves may be monolithic elastomer (PDMS) membrane valves. The system may be fabricated as described in the above-identified U.S. patent application Ser. No. 10/750,533, which has been incorporated by reference. As such, the system may include a four layer glass-glass-PDMS-glass stack that incorporates the microfluidic valves and pumps, the RTDs, the thermal cycling chambers, the clean-up and concentration chambers, and the CE channels.

The system 900, in one embodiment, includes 24 thermal cycling chambers, 24 purification chambers, and 24 CE channels arranged on a quadrant of a 150-mm diameter glass substrate. Each thermal cycling chamber (~250 nL) is isolated from the distribution channel by PDMS membrane valves (V1) 922. Rigid containment of the chamber volume with active valves is necessary for bubble-free loading and immobilization of a sample during thermal cycling since sample movement, bubble formation, and sample evaporation can seriously affect the performance.

The RTDs may be fabricated of titanium (Ti) and platinum (Pt). Different materials (Au, Al, Pt, Ni) using different metal deposition techniques, such as sputtering and both thermal and electron-beam evaporations, may be used to fabricate the heaters. Nickel heaters exhibit good heating uniformity, have good scratch resistance, show no noticeable degradation of performance even after hundreds of thermal cycles, and are easily fabricated. The microfabricated heaters and the thermal cycling chambers are positioned away from the CE microchannels to avoid evaporation of buffer in the cathode reservoirs and to minimize the heating of the injection region during thermal cycling. The resistive ring heaters can be fabricated on the back side of the bottom wafer to ensure good thermal transfer between the heaters and the chambers. The equally-spaced RTDs are integrated on the microplate to provide precise temperature sensing ensuring temperature uniformity across the heaters for optimal performance.

The thermal cycling chambers may be cycled with a LabVIEW program (National Instruments, Austin, Tex.). (LabView VI) Temperature control can be accomplished through a proportion/integration/differentiator (PID) module within the LabVIEW program.

In operation, in one embodiment, a sequencing separation matrix is introduced into the CE separation channels using positive pressure through the anode 910. A separation matrix fills the cathode reservoirs 912 and the waste reservoirs 914, as well as arms 924 connecting the cross-injection point to the associated sample purification chambers. The filling rate can be modulated through adjustment of the widths and lengths of the various interconnecting channels. The cathode and anode reservoirs, and the connecting arms may be filled at the same rate. Water, for example, is loaded from a loading (L) port 926 connected to the distribution channel 916 to fill the thermal cycling chambers 902 and the sample purification chambers 904 ensuring continuity for subsequent processes. An exit port (E) 936 is shared by both the thermal cycling chambers 902.

A capture gel matrix is loaded into the sample purification chambers through ports (F) 928. Libraries of clonal DNA beads that have been sorted and prepared using a FACS unit are loaded from the port 926 (valves (V1) 922 and (V2) 930 open, and valve (V3) 932 closed) using, for example, a syringe pump. A pressure transducer is employed in the inlet to monitor the head pressure. Auto-valves at the exit ports of the thermal cycling chambers will stop the flow into a chamber once a bead is trapped in the auto-valve as described above. As each auto-valve is filled with a bead in each thermal cycling chamber, the head pressure will continue to increase. In this manner, loading a bead in each thermal cycling chamber is achieved by monitoring the head pressure.

Upon filling the chambers, the valves (V2) 930 and (V1) 922 are closed and thermal cycling reactions initiated. Since the beads will be sorted directly in the thermal cycling cocktail, no additional steps are needed before thermal cycling. Alternatively, sorting could be performed in a buffer followed by introduction of the thermal cycling cocktail into the thermally cycling chambers to minimize reagent usage. The heaters 918a and 918b, as noted, drive the thermal cycling and sample purification reactions, and the reaction temperatures are monitored by the RTDs 920.

Thermal cycling products are driven to the purification chambers by applying an electric field across the port (L) 926 and a sample port or electrical contact point (S) 934 with the valves (V1) 922 and (V3) 932 open. Flushing of the non-captured reagents is performed by applying an electric field between the port (S) 934 and the port (F) 928. Thereafter, the sequencing products are injected from the purification chambers into the associated microchannels 908 for CE separation, by applying a potential between the port (S) 934 and the waste reservoir (W) 914. The rotary confocal fluorescence scanner is used to detect the sequencing samples. The scanner interrogates the channels sequentially in each rotation of the scanner head.

As shown, separations of the purified DNA sequencing products are achieved by using cross-injection. Alternatively, direct injection could be used.

In another embodiment, the microemulsion PCR approach of colony formation is replaced by a continuous flow through PCR technique in which bouli or droplets for performing single-molecule PCR amplification of templates are formed and then amplified. The bouli or plugs are formed, for example, by combining an aqueous solution of PCR reagents and dilute template fragments with a hydrophobic solution that acts as a carrier. The bolui produced by this technique will contain statistically a small number of copies of a sequencing template. Ideally the concentration is chosen so that only one in 10 bolui contain a single sequencing template. This mean that only one in 100 will simultaneously contain undesirably two templates. A microsphere or bead carrying one of the primers in the PCR reaction can also be entrained within a bolus or droplet in the process of performing this technique. Thus, a colony may comprise bolui carrying multiple clonal copies of a single sequencing template or bouli having microspheres carrying such copies.

Figure 10A:
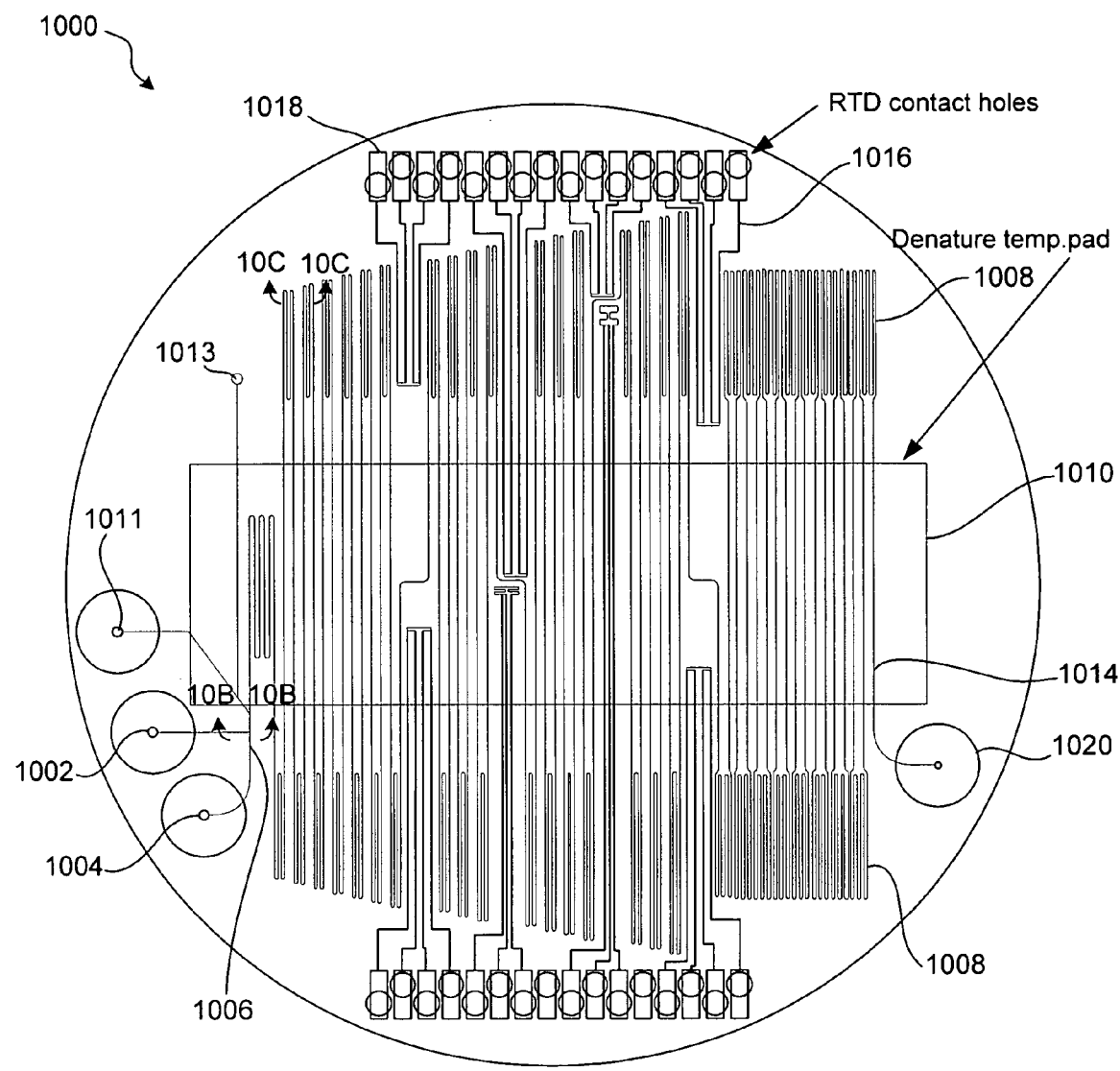
FIG. 10A is a diagrammatic representation of a continuous flow through PCR microfabricated device.
Figure 10B:
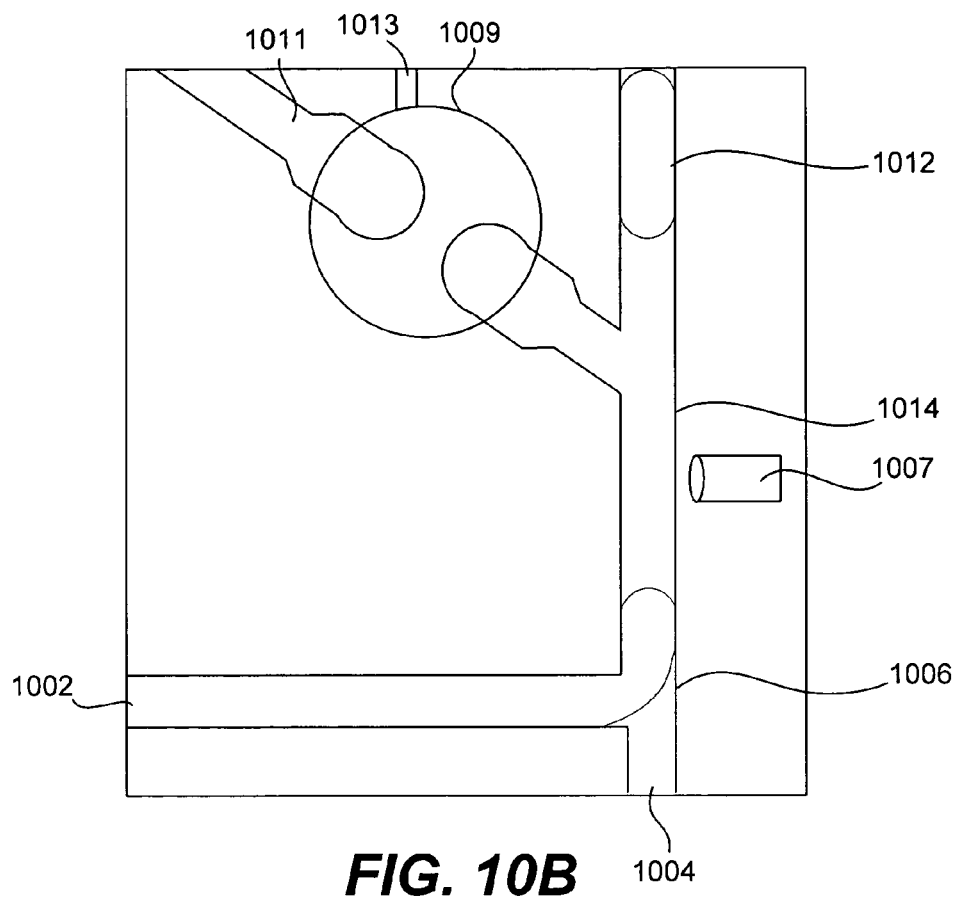
FIG. 10B is an enlarged view at lines 10B-10B of FIG. 10A, illustrating a "T"-injector region of the microfabricated device.
Figure 10C:
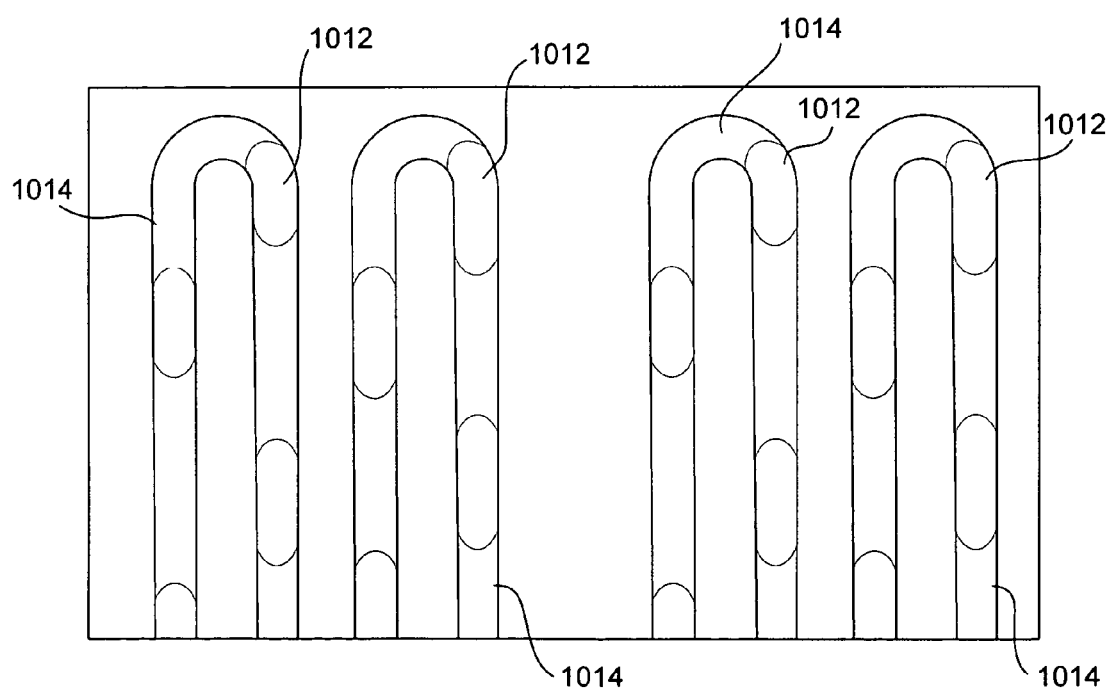
FIG. 10C is an enlarged view at lines 10C-10C of FIG. 10A, illustrating a portion of the channels of the microfabricated device.

As shown in FIGS. 10A, 10B, and 10C, a continuous flow through microfabricated PCR system 1000 includes ports 1002 and 1004. An aqueous solution of microspheres, PCR reagents and template fragments, in one embodiment, is introduced into a "T"-injector region 1006 via the port 1002, while a hydrophobic carrier solution is introduced into the "T"-injector region via the port 1004. A bolus or droplet 1012 containing a microsphere is thus formed downstream of the "T"-injector region.

The system 1000 further includes an optical sensor 1007 (FIG. 10B) located downstream of the "T"-injector near an input end of a channel 1014. The sensor may comprise a focused laser beam and a photodiode to detect off-axis light scattering.

The sensor is configured to select a bolus that contains a bead and to reject bolui with no bead or with more than one bead. A rejected bolus is passed out of the system via a valve 1009 and a waste port and channel 1011. The valve 1009 may be a four-layer PDMS valve that when open allows a rejected bolus to exit the system via the waste port 1011. The valve may be activated via a valve actuation port 1013. Since the fluidic resistance of the continuous flow system is so great, no valve is needed in the main channel 1014.

The system 1000 is designed for two-step PCR where the anneal and extend steps are combined. As such, the system includes two temperature zones 1008 and 1010 through which droplets 1012 pass via the flow through channels 1014. The device 1000 includes RTDs 1016 and associated RTD contact pads 1018 for monitoring the temperature of the different temperature zones. A bolus and microsphere, after undgergoing two-temperature PCR, exit the system via an exit port 1020.

As discussed, the microsphere can be treated with an intercalation dye, such as TO, that is nonfluorescent until intercalated into double-stranded DNA. Therefore, the microspheres that have amplified DNA can be identified by, for example, the FACS technique after they pass through the port 1020. Thereafter, the microspheres are introduced into a distribution channel of a device like the device 900 (See FIGS. 9A and 9B). The microspheres that do not have amplified DNA, on the other hand, will be disposed of.

The continuous flow through PCR system 1000, in one example, uses nanoliter droplets of PCR reagents suspended in a perfluorohydrocarbon carrier. See, Song, H., et al., "A microfluidic system for controlling reaction networks in time", *Angewandte Chemie—International Edition* 42, 768-772 (2003), which is hereby incorporated by reference. Droplets containing microspheres, PCR reagents, and template fragments, separated from one another by an immiscible liquid, are formed at the microfabricated T-injector 1006. Thereafter, the droplets flow through the regions 1008 and 1010 of the device that are held at anneal-extend-denature temperatures. The lengths of the channels 1014 in the different temperature zones 1008 and 1010 are selected based on required residence times at those temperatures. The cross-section of the channels and the desired flow rates are chosen to achieve stable droplet formation. The parameters of the device may be set to achieve a hot start at the denature temperature for 90 seconds, followed by anneal/extend for 45 seconds with a 1 second auto-extend for 35 cycles and a denature time of 15 seconds. The last 15 cycles may be configured to have a constant anneal/extend time of 80 seconds.

The device 1000 may comprise two 1.1-mm thick by 10-cm diameter borofloat glass wafers. The channels on the patterned wafer may have a D-shape cross-section with a width of about 210 μm and a depth of about 95 μm. On the other wafer, Ti/Pt RTDs may be fabricated for monitoring temperature gradients at different points in the device. Holes may be drilled for accessing the channels, and the two wafers may be thermally bonded to each other to form enclosed channels. The nanoports 1002 and 1004 are used to interface the device with micro-liter syringes through PEEK tubing. The glass surface of the channels may be rendered hydrophobic through silanization with 1H,1H,2H,2H-perfluorodecyl-trichlorosilane, based on a procedure published by Srinivasan et al., "Alkyltrichlorosilane-based self-assembled monolayer films for stiction reduction in silicon micromachines", *Journal of Microelectromechanical Systems* 7, 252-260 (1998), which is hereby incorporated by reference. Two syringe pumps may be used to dispense water and a 10:1 mixture of perfluorodecalin (mixture of cis and trans, 95%, Acros Organics, New Jersey, USA) and 1H,1H,2H,2H-perfluorooctanol (Acros Organics, New Jersey, USA) at a flow rate of 0.5 μl/min each. FIG. 10B shows the droplet formation process at the T-injector at about 1 droplet/s, and FIG. 10C shows the droplets as they move through the channel.

The technique, in one embodiment, uses microbeads in 10 nL droplets. Throughput is maintained at one in ten droplets containing both a single template molecule and a single bead. The aqueous PCR mix is prepared such that there is one template molecule per 100 nL of mix, corresponding to one molecule for every ten droplets. Also in the PCR mix are microbeads at a concentration of one per 10 nL of mix, corresponding to one bead for every droplet on average. As dictated by the Poisson distribution, 37% of the 10 nL droplets will contain only one microbead, the remaining containing either none or two plus. Each droplet, as discussed, is then optically scanned to determine the number of beads it contains. If the droplet does not contain a single microbead, the valve 1009 is opened, passing the droplet to waste. Approximately one third of the droplets will contain a single bead and are routed to the main channel; thus, the average flow rate is equal to about 1 droplet every 1.5 s. As such, every droplet in the main channel contains a single microbead, and one in ten also contains a single template molecule.

At the end of the device 1000, the droplets may be collected at the port 1020 via a standard capillary into a microfuge tube. The droplets are broken through centrifugation. Microbeads are collected and washed in 1× TE, again through centrifugation. The microbeads are routed into the thermal cycling chambers of the device 900 by either autovalving or active valving with on-chip detection. On-chip detection may comprise the use of an optical scanner or a timing arrangement that determines when a microsphere is located adjacent to an inlet of a thermal cycling chamber. The optical scanner, as discussed, may use bead light scattering to determine the location of a microsphere within the distribution channel. The timing arrangement is based on the fact that the fluid in the distribution channel is incompressible. As such, the location of a micropshere within the distribution channel, for instance, adjacent to an inlet of a thermal cycling chamber, can be calculated from the time that the microsphere has been in the distribution channel. This is advantageous because the valved entrances to each of the 96 inputs from the distribution channel, for example, can be actuated by a single pneumatic input. Also the pneumatic input is not actuated until a detected bead is flowed directly opposite a reactor that does not have a bead yet.

To demonstrate the feasibility of generating sequencing templates using two-temperature PCR, high-temperature primers were designed and tested in a conventional thermal cycler. Two primers, M13_2T_F-5'TTCTGGTGCCG-GAAACCAGGCAAAGCGCCA-3'(SEQ. ID NO. 2) $T_m$=70.3° C. and M13_2T_R 5'-ACGCGCAGCGTGAC-CGCTACACTTGCCA-3' (SEQ. ID NO. 3) $T_m$=70.7° C. were designed to generate a 943 by amplicon from the M13 genome. To approximate the concentration of a single template molecule in a 11 nL emulsion compartment, 18.75 femtograms of M13 template were cycled in a 25 uL PCR reaction (94° C. 1.5 min followed by 50 cycles of 94° C. 10 s, 70° C. 30 s with an auto-extend of 1 s/cycle). The resulting amplicon was a single clean peak at the expected size with a yield of about 40 ng/uL.

If such a system is used to amplify genomic DNA, for 1× coverage and average fragment size of 1000 bps, about 3 million fragments need to be amplified. The probability that two different fragments end up in a single droplet can be reduced to less than 0.01 by diluting the fragments in the PCR reagent such that on an average one in ten droplets contains a fragment. Hence, the system will have to process 30 million droplets. This device is designed to generate one droplet about every 1.5 seconds. If 20 such devices are run in parallel, the entire genome can be amplified and interfaced with a bank of the sequencing systems 900 to produce 1× coverage in only one month.

While the invention has been particularly shown and described with reference to specific embodiments, it will also be understood by those skilled in the art that changes in the form and details of the disclosed embodiments may be made without departing from the spirit or scope of the invention. For example, the embodiments described above may be implemented using a variety of materials. Therefore, the scope of the invention should be determined with reference to the appended claims.

What is claimed is:

1. A microfabricated structure comprising a distribution channel and a plurality of second channels integrated on the microfabricated structure and further comprising a plurality of microcarrier elements, wherein:
   (a) each of the second channels is connected to the distribution channel;
   (b) the distribution channel is configured to distribute the plurality of microcarrier elements, each carrying multiple clonal copies of a sequencing template, into a plurality of second channels;
   (c) each of the plurality of second channels comprises a thermal cycling reactor connected to a purification chamber connected to a component separation channel;
   (d) each of the thermal cycling reactors is configured to produce thermal cycling extension fragments from a microcarrier element located therein, the purification chambers are configured to capture and concentrate the extension fragments and the component separation channels are configured to separate the extension fragments from each other based on their relative sizes; and
   (e) the microfabricated structure is configured such that only one microcarrier element can pass into a particular thermal cycling reactor during distribution of the plurality of microcarrier elements from the distribution channel; wherein the distribution channels, thermal cycling reactors and component separation channels are integrated on the same microfabricated structure.

2. The microfabricated structure of claim 1 further comprising a timing mechanism and valving that together are configured to permit one of the plurality of microcarrier elements flow into a thermal cycling reactor that does not already contain a microcarrier element and to prevent any of the plurality of microcarrier elements from flowing into any thermal cycling reactor that already contains one of the plurality of microcarrier elements.

3. The microfabricated structure of claim 1 wherein each of the plurality of microcarrier elements comprises a microsphere carrying the multiple copies of the sequencing template.

4. The microfabricated structure of claim 3 wherein the diameter of the microsphere is between about 1 and 100 microns.

5. The microfabricated structure of claim 4 wherein the diameter of the microsphere is about 10 microns.

6. The microfabricated structure of claim 1 wherein the sequencing template is a DNA or RNA sequencing template.

7. The microfabricated structure of claim 1 wherein each component separation channel comprises a capillary electrophoresis channel.

8. The microfabricated structure of claim 1 further comprising an autovalve at an exit port of each thermal cycling reactor.

9. The microfabricated structure of claim 8 wherein the autovalve comprises a constriction that is configured to trap the micro carrier element in the thermal cycling reactor and to substantially block further flow into the thermal cycling reactor.

10. The microfabricated structure of claim 9 wherein the shape of the constriction is substantially circular.

11. The microfabricated structure of claim 9 wherein the shape of the constriction is substantially semicircular.

12. The microfabricated structure of claim 8 wherein the autovalve comprises a first valve located in an inlet channel in fluid communication with the thermal cycling reactor and a second valve located in the exit port.

13. The microfabricated structure of claim 12 wherein in operation the second valve is configured to close before the first valve to move a microcarrier element out of the constriction and into a main body portion of the thermal cycling reactor before thermal cycling.

14. The microfabricated structure of claim 1 further comprising least one of an optical detector and a timing mechanism.

15. The microfabricated structure of claim 14 wherein the optical detector comprises an optical scanner that detects light from a microcarrier element.

16. The microfabricated structure of claim 1 wherein the microfluidic structure comprises a plurality of valves and an elastomer membrane, wherein applying pneumatic pressure or vacuum on the membrane actuates the valves.

* * * * *